(12) United States Patent
Greenberger

(10) Patent No.: US 6,887,856 B1
(45) Date of Patent: *May 3, 2005

(54) PROTECTION FROM IONIZING IRRADIATION OR CHEMOTHERAPEUTIC DRUG DAMAGE BY IN VIVO GENE THERAPY

(75) Inventor: Joel S. Greenberger, Sewickley, PA (US)

(73) Assignee: University of Pittsburgh, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 08/907,041

(22) Filed: Aug. 6, 1997

Related U.S. Application Data

(63) Continuation of application No. 08/484,836, filed on Jun. 7, 1995, now abandoned, and a continuation of application No. 08/136,079, filed on Oct. 15, 1993, now Pat. No. 5,599,712.

(51) Int. Cl.$^7$ .................. A01N 43/04; A01N 63/00; C12N 15/00; C12N 15/63; C07G 17/00

(52) U.S. Cl. ............ 514/44; 435/267; 435/320.1; 435/455; 424/93.2; 424/93.21

(58) Field of Search .................. 514/44, 2; 435/267, 435/320.1, 455, 172.1, 172.2, 172.3, 240.2, 240.1, 91.1, 91.2, 93.21; 424/93.2, 93.21

(56) References Cited

U.S. PATENT DOCUMENTS

| | | | | |
|---|---|---|---|---|
| 4,751,180 A | * | 6/1988 | Cousens et al. | 435/68 |
| 4,980,286 A | | 12/1990 | Morgan et al. | 435/172.3 |
| 5,240,847 A | * | 8/1993 | Heckl et al. | 435/189 |
| 5,334,383 A | * | 8/1994 | Morrow | 424/94.4 |
| 5,599,712 A | * | 2/1997 | Greenberger | 435/267 |
| 5,670,488 A | * | 9/1997 | Gregory et al. | 514/44 |
| 6,221,848 B1 | * | 4/2001 | Greenberger | 514/44 |

FOREIGN PATENT DOCUMENTS

| | | | |
|---|---|---|---|
| EP | 0284105 | * | 3/1988 |
| WO | 93/12756 | | 7/1993 |
| WO | WO 94/19493 | * | 9/1994 |
| WO | WO 94/21283 | * | 9/1994 |

OTHER PUBLICATIONS

Ishiye et al., Oct. 15, 1992, FEMS Microbiology Letters, vol. 97, p. 235–241.*
Branch et al., 1993, American Review of Respiratory Disease, vol. 147, No. 4, Supp. S, pp. A206.*
Nabel et al., 1994, Annals New York Academy of Sciences, vol. 714, p. 247–252.*
Eck et al.; Gene–Based Therapy, 1996, The Pharmacological Basis of Therapeutics:77–101.*
Deonarain; Ligand–targeted receptor–mediated vectors for gene delivery, 1998, Exp. Opin. Ther. Patents 8:53–69.*
Verma et al.; Gene therapy– promises, problems and prospects, 1997, Nature, vol. 389: 239–242.*
Mastrangelo et al., Seminars in Oncology vol. 23(1), p. 4–21, Feb. 1996.*
Orkin et al., Report and Recommendatioins of the Panel to Assess the NIH Investment in Research on Gene Therapy, Dec. 1995.*
Alton et al., Nature Genetics, 5:135–142, 1993.*
Hockenberry et al., Cell, 75:241–251, 1993.*
Jaffe et al., Nature Genetics, 1:372–378, 1992.*
Jolly, Cancer Gene Therapy, 1(1):51–64, 1994.*
Mulligan, Science, 260:926–932, 1993.*
Petkau, Cancer Treatment Rev., 13:17–44, 1986.*
Sorrentino et al., Science, 257:99–103, 1992.*
Wu et al., J. Biol. Chem., 263 14621–14624, 1988.*
Ledley, F.D., Human Gene Therapy, 2:77–83 (1991).*
Ledley, F.D., Current Opinion in Biotechnology, 5:626–636, 1994.*
Lehrer et al., Carcinogenesis 10(12):2279–84, 1989.*
Matsubara J. et al., Pharmac. Ther., 39:331–333, 1988.*
Marshall, Science, 269, 1995, 1050–1055.*
"NIH Report and Recommendations", Dec. 7, 1995, 1–40.*
Xiang, K., "Multiple Taq I RFLPs at the Human Manganese Superoxide Dismutase (S0D2) locus on Chromosome 6", *Nucleic Acids Research*, vol. 15, No. 18 (1987).
Hyland, V. J. et al., "A 5' Flanking Region of the Metallothionein, MT2A, Gene Identifies Two Moderately Frequent RFLPs", *Nucleic Acids Research*, vol. 15, No. 3 (1987).
Karin, M. et al., "Human Metallothionein Genes–Primary Structure of the Metallothionein–II Gene and a Related Processed Gene", *Nature*, vol. 299 (Oct. 28 1982).
Sherman, L. et al., "Nucleotide Sequence and Expression of Human Chromosome 21–encoded Superoxide Dismutase mRNA", *Proc. Natl. Acad. Sci. USA*, vol. 80, pp 5465–5469 (Sep. 1983).
Richards, R. I. et al., "Structural and Functional Analysis of the Human Metallothionein–$I_A$ Gene: Differential Induction by Metal Ions and Glucocorticoids", *Cell*, vol. 37, pp 263–272 (May 1984).
Lieman–Hurwitz, J. et al., "Human Cytoplasmic Superoxide Dismutase cDNA Clone: A Probe for Studying the Molecular Biology of Down Syndrome", Proc. Natl. Acad. Sci. USA, vol. 79, pp 2808–2811 (May 1982).

(Continued)

Primary Examiner—Shin-Lin Chen
(74) Attorney, Agent, or Firm—Foley & Lardner LLP

(57) ABSTRACT

A method of protecting a subject against an agent that elicits production of toxic free radicals, superoxide anions, or heavy metal cations in the subject is disclosed which entails in vivo administration to the subject of a polynucleotide encoding a protein that is transiently expressed in said subject. The transiently expressed protein is capable of neutralizing or eliminating the toxic free radicals, superoxide anions or heavy metal cations that are elicited by the agent. The method is particularly useful in protecting cancer patients against the damaging effects of ionizing radiation and chemotherapeutic drugs. A composition useful in carrying out the method also is disclosed.

29 Claims, 7 Drawing Sheets

OTHER PUBLICATIONS

Cai, D. W. et al., "Stable Expression of the Wild–Type p53 Gene in Human Lung Cancer Cells After Retrovirus–Mediated Gene Transfer", Proceedings of the American Association of Cancer Research, vol. 34, p 505, 3011 (Mar. 1993).

McCormick, M. L. et al., "Superoxide Dismutase and Catalase Levels During Estrogen–Induced Renal Tumorigenesis, in Renal Tumors and their Autonomous Variants in the Syrian Hamster", Carcinogenesis, vol. 12, No. 6, pp 977–983 (1991).

Engelhardt, J. et al., "In Vivo Retroviral Gene Transfer into Human Bronchial Epithelia of Xenografts", The American Society for Clinical Investigation, Inc., vol. 90, pp 2598–2609 (Dec. 1992).

Oberley, L. W. et al., "Transfection of Manganese Superoxide Dismutase cDNA into Cultured Tumor Cells," Proc. Amer. Assoc. for Canc. Res., Abstract 98 (1993).

Yang, Y. et al., "An Approach for Treating the Hepatobillary Disease of Cystic Fibrosis by Somatic Gene Transfer", Proc. Natl. Acad. Sci. USA, vol. 90, pp 4601–4605 (May 1993).

Rosenfeld, M. A. et al., "Adenovirus–Mediated Transfer of a Recombinant α1–Antitrypsin Gene to the Lung Epithelium in Vivo", Reports, pp 431–434 (Apr. 19, 1991).

Dunn, M. A. et al., "MINIREVIEW—Metallothionein (42525A)", Proceedings of the Society for Experimental Biology and Medicine 185, pp 107–119 (1987).

Lohrer, H. et al., "Overexpression of Metallothionein in CHO Cells and its Effect on Cell Killing by Ionizing Radiation and Alkylating Agents", Carcinogenesis, vol. 10, No. 12, pp 2279–2284 (1969).

Holland, C. et al., "Enhancer Sequences of a Retroviral Vector Determine Expression of a Gene in Multi–potent Hematopoietic Progenitors and Committed Erythroid Cells", Proc. Natl. Acad. Sci. USA, vol. 84, pp 8662–8666 (Dec. 1987).

Roth, J. et al., "p53 Regulates the Transcription of Human Cytokeratin β Gene in Human Lung Cancer Cell Lines", Proceedings of The American Association for Cancer Research, vol. 34, p 509 (Mar. 1993).

Petkau, A., "Scientific Basis for the Clinical Use of Superoxide Dismutase", Cancer Treatment Reviews 13, pp 17–44 (1986).

Fujiwara, T. et al., "Retroviral–Mediated Transduction of p53 Gene Regulates TGF–β Gene Expression and Secretion in a Human Glioblastoma Cell Line", Proceedings of the American Association for Cancer Research, vol. 34, p 449, 2680 (Mar. 1993).

Georges, R. N. et al., "In–Vivo Retroviral Transduction of Antisense K–ras Suppresses Tumor Growth in an Orthotopic Lung Cancer Model", Proceedings of the American Association for Cancer Research, vol. 34, p 336 (Mar. 1993).

Shiraishi, N. et al., "Elevation in Metallothionein Messenger RNA in Rat Tissues After Exposure to X–Irradiation", Toxicology and Applied Pharmacology 98, pp 501–506 (1989).

Flotte, T. et al., "Gene Expression from Adeno–Associated Virus Vectors in Airway Epithelial Cells", Am. J. Respir. Cell Molec. Biol, 7:349 (1992).

Anklesaria, P. et al., "Engraftment of a Clonal Bone Marrow Stromal Cell Line in vivo Stimulates Hemato–poietic Recovery from Total Body Irradiation", Proc. Natl. Acad. Sci. USA, vol. 84, pp 7681–7685, (Nov. 1987).

Armstrong, J. G. et al., "Three Dimensional Conformal Radiation Therapy May Improve the Therapeutic Ratio of High Dose Radiation Therapy for Lung Cancer", Int. J. Radiation Oncology Biol. Phys., vol. 00, pp 001–005 (1993).

Georges, R. N. et al., "Prevention of Orthotopic Human Lung Cancer Growth by Intratracheal Instillation of a Retroviral Antisense K–ras Construct", Cancer Research 53, pp 1743–1746 (Apr. 15, 1993).

Stribling, R., "Aerosol Gene Delivery in vivo", Proc. Natl. Acad. Sci. USA, vol. 89, pp 11277–11281, (Dec. 1992).

Ferkol, T. et al., "Regulation of the Phosphoenolpyruvate Carboxykinase/human Factor IX Gene Introduced into the Livers of Adult Rats by Receptor–Mediated Gene Transfer", Methodology, vol. 7, pp 1081–1091, (Aug. 1993).

Rosenfeld, M. et al., "In Vivo Transfer of the Human Cystic Fibrosis Transmembrane Conductance Regulator Gene", Cell, vol. 68 (Jan. 10, 1992).

Mulligan, R., "The Basic Sciences of Gene Therapy", Science, vol. 260, pp 926–932 (May 14, 1993).

Ledley, FD Clinical Considerations in the Design of Portocols for Some.

Hallahan et al."Protein Kinase C Mediates X–ray Inducibility of Nuclear Signal Transducers EGR1 and JUN," Proc. Natl. Acad. Sci. USA 88:2156–2160 (Mar. 1991).

Datta et al."Ionizing Radiation Activates Transcription of the EGR1 Gene via CArG Elements," Proc. Natl. Acad. Sci. USA 89:10149–10153 (Nov. 1992).

S. Kim et al., "Transcriptional Targeting of Replication–defective Adenovirus Transgene Expression to Smooth Muscle Cells In Vivo", J. Clin. Invest., vol. 100, No. 5, Sep. 1997, p. 1006–1014.

Y.J. Kang et al., "Overexpression of Metallothionenin in the Heart of Transgenic Mice Suppresses Doxorubicin Cardiotoxicity", J. Clin. Invest., vol. 100, No. 6, Sep. 1997, p. 1501–1506.

J. Greenberger, "Prevention of Late Effects of Irradiation Lung Damage By Manganese Superoxide Dismutase Gene Therapy", Gene Therapy: Final Revised, p. 1–43.

* cited by examiner

PROTECTION FROM IONIZING IRRADIATION OR CHEMOTHERAPEUTIC DRUG DAMAGE BY IN VIVO GENE THERAPY

This application is a continuation of U.S. application Ser. No. 08/484,836, filed Jun. 7, 1995 (now abandoned), and a continuation of U.S. application Ser. No. 08/136,079, filed Oct. 15, 1993 (now U.S. Pat. No. 5,599,712).

BACKGROUND OF THE INVENTION

The present invention is directed generally to protecting an individual's tissues and cells against the damaging effects of an agent that elicits the production of a free radical, superoxide anion, or heavy metal cation when that individual is exposed to the agent. Specifically, the invention is directed to obtaining this protection by transient expression of a protective protein through somatic gene transfer in vivo.

Therapeutic concentrations of anti-cancer drugs and clinical radiation therapy are known to damage a patient's normal tissues and cells. A need clearly exists for means to protect a patient's normal tissues during chemotherapy and/or radiation therapy. Previous methods of affording such protection include administration of sulfhydryl compounds such as thiols or other radical scavenger compounds.

The major way in which radiation damages biomolecules and cells is through its interaction with water to produce toxic free radicals ($H^{\bullet}$, $OH^{\bullet}$, $e_{aq}^{-}$) and $H_2O_2$ or, through interaction with oxygen, to produce the superoxide radicals ($^{\bullet}O_2^{-}$). In the late 1940's it was discovered that sulfhydryl compounds, such as cysteine and cysteamine, provide radiation protection in animals. Patt et al., Science 110: 213 (1949). Thiol groups scavenge radiation-produced free radicals by donating a hydrogen atom to damaged molecules. Despite extensive efforts to develop more effective protective agents, no thiol-based radioprotector has been found to be significantly better than cysteamine. Mitchell et al., Arch. Biochem. and Biophys. 289: 62 (1991). However, the use of thiol drugs to protect against radiation damage is limited by the toxicity of such compounds.

Antineoplastic agents, particularly the class of chemotherapeutic drugs known as alkylating agents, also produce free radicals that are cytotoxic due to their ability to form covalent bonds with nucleic acids. Most alkylating agents form positively charged carbonium ions that yield the charged alkylating intermediate $R-CH_2-CH_2^{+}$ which attacks electron-rich sites on nucleic acids, proteins, small molecules and amino acids.

Several endogenous intracellular scavengers of free radicals, superoxide radicals and heavy metal cations have been identified. Induction or elevated activities of each of metallothionein (MT), gamma-glutamyl transpeptidase ($\gamma$-GTP) and superoxide dismutase (SOD) are known to provide resistance to ionizing radiation damage in vitro. Since these proteins function intracellularly to scavenge free radicals, superoxide anions or heavy metal cations, these proteins need to be provided or induced intracellularly. Administration of these proteins directly cannot provide continual levels of the intracellular quantities required to furnish protection against ionizing radiation or an anticancer agent. Furthermore, if metallothionein, superoxide dismutase or gamma glutamyl transpeptidase proteins are administered to cells extracellularly, they may be rapidly degraded by proteases and fail to function intracellularly. No method for providing functional intracellular therapeutic levels of metallothionein, superoxide dismutase or gamma glutamyl transpeptidase to normal tissues in vivo is known.

SUMMARY OF THE INVENTION

It therefore is an object of the present invention to provide a method of protecting normal cells against the damaging effects of an anticancer agent or ionizing radiation by providing genes encoding protein protective to normal somatic cells.

It is a further object of this invention to provide a safe and efficient method of transferring oxidation or cation-scavenging protein encoding genes directly into a patient's cells.

It is yet another object of this invention to transfer oxidation or cation-scavenging protein encoding genes directly into a patient's cells using an easily administrable method.

Another object of the present invention is to provide transient expression of the oxidation or cation-scavenging protein in the cells to be protected against the anticancer agent, wherein either the transferred polynucleotide or gene is cleared after therapeutic courses of ionizing radiation therapy or chemotherapy, or the transferred polynucleotide or gene is stably integrated within the genome, but its expression is temporary, and induced for a limited time by the ionizing radiation therapy or chemotherapy.

In accomplishing these and other objects, there has been provided, in accordance with one aspect of the present invention, a method for protecting a subject against an agent, typically a chemotherapeutic agent, that elicits production of a toxic species when the subject is exposed to the agent, wherein the toxic species are a free radical, a superoxide anion, or a heavy metal cation. In a preferred embodiment of the invention, the method comprises the step of administering to a subject in vivo a pharmaceutical composition comprising: (A) a polynucleotide that encodes a protein that is transiently expressed in the subject, wherein the protein is capable of neutralizing or eliminating the toxic species; and (B) a pharmaceutically acceptable vehicle for the polynucleotide. The agent may be ionizing radiation, clinical radiation therapy, or a chemotherapeutic drug.

In a preferred embodiment of the invention, the proteins of the invention that are capable of neutralizing or eliminating the toxic species can be gamma glutamyl transpeptidase, manganese superoxide dismutase, or metallothionein.

In further embodiments of the invention, the pharmaceutical composition can be dispensed to the subject through inhalation, parenteral administration, intrarectal administration or intravesicle administration. In another embodiment, the gene or polynucleotide is introduced ex vivo (Andersen, W. F. et al., U.S. Pat. No. 5,399,346, 1995.) into hematopoietic cells. In an embodiment of the invention, administration of the pharmaceutical composition may be performed prior to a subject's exposure to an agent.

In yet another embodiment of the invention, the pharmaceutically acceptable vehicles for the polynucleotide of the invention can be liposomes, an adenovirus vector, or ligand-DNA conjugates, or a hematopoietic progenitor cell transfected in vitro with said polynucleotide(s) or gene(s) by use of either chemical transformations or electroporation. In still another embodiment of the invention, the pharmaceutical composition of the invention comprises a mixture of polynucleotides selected from a polynucleotide encoding gamma glutamyl transpeptidase, a polynucleotide encoding manganese superoxide dismutase or a polynucleotide encoding metallothionein. Alternatively, the pharmaceutical composition of the invention can comprise a polynucleotide encoding gamma glutamyl transpeptidase, a polynucleotide encoding manganese superoxide dismutase or a polynucleotide encoding metallothionein.

In another embodiment of the invention, a suitable subject can be a cancer patient. In a further embodiment, a suitable cancer patient subject may be a lung cancer patient, prostate cancer patient, cervical cancer patient, endometrial cancer patient, ovarian cancer patient, or bladder cancer patient.

Another aspect of the invention is directed to a pharmaceutical composition comprising a polynucleotide that encodes a protein that is transiently expressed in a subject exposed to an agent that elicits production of a toxic species, such as a free radical, a superoxide anion, or a heavy metal cation, wherein the protein is capable of neutralizing or eliminating the toxic species; and a pharmaceutically acceptable vehicle for the polynucleotide. The polynucleotide in such a composition of the invention can be a polynucleotide encoding gamma glutamyl transpeptidase, a polynucleotide encoding manganese superoxide dismutase or a polynucleotide encoding metallothionein. The pharmaceutically acceptable vehicle in such a composition of the invention can be a liposome, an adenovirus vector, a ligand-DNA conjugate, or in vitro transformed human cells.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A illustrates the Wild-type Adenovirus type 5 (Ad5) genome showing the E1a, E1b and E3 regions and the portion to be deleted from the left end of Ad5 for insertion of the appropriate expression cassettes. An expression cassette is a nucleic acid construct that includes, as operably linked components in the direction of transcription, a transcriptional initiation region, a nucleic acid sequence encoding a protein of interest and a transcriptional termination region wherein the transcriptional regulatory regions are functional in the targeted mammalian host cell. FIG. 1B illustrates an expression cassette containing regulatory sequences and a recombinant DNA sequence encoding metallothionein.

FIG. 2A illustrates the Wild-type Adenovirus type 5 (Ad5) genome showing the E1a, E1b and E3 regions and the portion to be deleted from the left end of Ad5 for insertion of the appropriate expression cassettes. FIG. 2B illustrates an expression cassette containing regulatory sequences and a recombinant DNA sequence encoding γ-GTP.

FIG. 3A illustrates the Wild-type Adenovirus type 5 (Ad5) genome showing the E1a, E1b and E3 regions and the portion to be deleted from the left end of Ad5 for insertion of the appropriate expression cassettes. FIG. 3B illustrates an expression cassette containing regulatory sequences and a recombinant DNA sequence encoding manganous superoxide dismutase.

DETAILED DESCRIPTION OF THE INVENTION

Figure 1A:
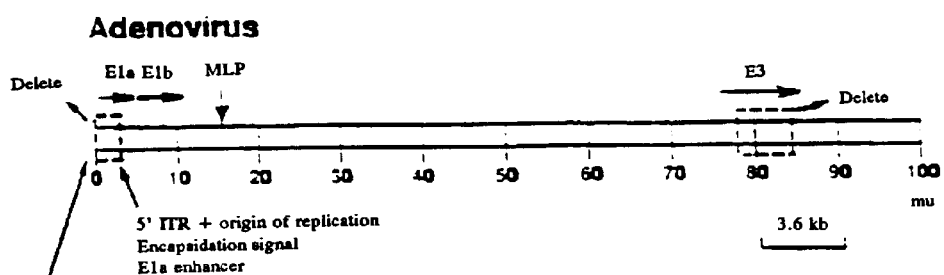
FIGS. 1A and 1B are schematic drawings of the construction of a Metallothionein (MT) recombinant adenovirus vector (Ad-MT) of the present invention.

Ionizing radiation produces toxic free-radical species. Antineoplastic agents, particularly the class of chemotherapeutic drugs known as alkylating agents, also produce free radicals that are cytotoxic because of their ability to form covalent bonds with nucleic acids. Most alkylating agents, including cyclophosphamide, nitrogen mustard, melphalan, chlorambucil, busulfan, nitrosourea, cis-platinum, streptozotocin, aziridinylbenzoquinone (AZQ), dicarbazine (DTIC), mAMSA and mitoxantrone, form positively charged carbonium ions that yield a charged alkylating intermediate R—$CH_2$—$CH_2$+that attacks electron-rich sites on nucleic acids, proteins, small molecules and amino acids. Chabner et al., in CANCER; PRINCIPLES AND PRACTICE OF ONCOLOGY, 2nd edition, DeVita et al. (eds.) (J. B. Lippincott Co., Philadelphia 1985).

The method of the present invention provides a means for protecting an individual against an agent that elicits the production of a free radical, a superoxide anion, and/or a heavy metal cation. The method of the present invention employs gene therapy, which is the transfer of genetic material into specific cells of a patient. Ex vivo gene therapy is gene therapy that involves the removal of the relevant target cells from the body, transduction of the cells in vitro, and subsequent reintroduction of the modified cells into the patient. Transient gene expression, according to the present invention, can result by one of two mechanisms:

(A) The method of gene transfer introduces DNA sequences into the nucleus in an unintegrated form. In that case, transient expression, or nonintegrated expression is limited by the stability of the nonintegrated DNA molecule (s) and may persist for extended periods of time, but rarely persists for periods longer than about one to three weeks;

(B) Alternatively, the gene or polynucleotide may be stably integrated into the genome. Transient expression is achieved by virtue of an inducible transcriptional promoter to control the expression of the gene or polynucleotide. In a preferred embodiment, the inducible promoter is induced directly or indirectly by the ionizing radiation therapy or chemotherapy agent itself.

In a preferred embodiment, hematopoietic cells removed from the patient are transformed with a suitable plasmid by any of the transformation methods known to one trained in the art. The transformation can lead to stable integration of the plasmid containing any combination of the polynucleotide(s) or gene(s) discussed above. The transcription of those polynucleotide(s) or gene(s), according to this embodiment, is controlled by the erg1 promoter, a promoter induced by irradiation. Hallahan, D.E.; Sukhatme, V.P.; Sherman, M.L.; Subbulakshmi, V.; Kufe, D.; Weichselbaum, R. R., "Protein kinase C mediates x-ray inducibility of nuclear signal transducers erg-1 and JUN. *Proc. Natl. Acad. Sci. USA* 88:2156–2160 (1991) and Datta, R.; Rubin E.; Sukhatme, V.; Qureshi, S.; Hallanhan, D.; Weichselbaum, R.R.; Kufe, D.W., "Ionizing radiation activates transcription of the egr-1 gene via CArG elements. *Proc. Natl. Acad. Sci. USA* 89:10149–10153 (1992). In that case, transcription of the polynucleotide(s) or gene(s) controlled by erg-1 will stop somewhere between 60 and 90 hours post induction.

The gene therapy method of the present invention involves an in viva method of gene therapy that provides a polynucleotide encoding a protein capable of neutralizing or eliminating a toxic free radical, superoxide anion and/or heavy metal cation, wherein the protein is transiently expressed in the individual. The transgenes of the present invention encode protein(s), such as metallothionein, superoxide dismutase or gamma glutamyl transpeptidase, that scavenge a toxic free radical, superoxide anion and/or heavy metal cation.

A gene that is transferred to an individual is called a transgene. The method of the present invention can be used to protect specific organs in cancer patients against the damaging effects of ionizing radiation and chemotherapeutic drugs, which produce free radicals, superoxide anions, and/or heavy metal cations. In particular, the method of the present invention can be used to transfer a gene to normal lung tissue cells prior to clinical radiation therapy or chemotherapeutic drug administration to combat cancer. Also, the method of the present invention can be used to transfer a gene to normal bladder or rectal cells prior to clinical radiation therapy or chemotherapeutic drug administration to combat prostate, bladder, cervical or endometrial cancer.

In one embodiment, the method of the present invention is directed toward transient in vivo gene therapy to lung cancer patients to provide protection of normal lung tissue when the lung cancer is treated with ionizing radiation therapy or anti-neoplastic alkylating agents. Aerosol administration or inhalation therapy that provides a transgene to the lungs is a preferred method of in vivo gene therapy when targeting genetic material to the lungs. In another embodiment, the method of the present invention is directed toward transient in vivo gene therapy to prostate, bladder, cervical or endometrial cancer patients to provide protection to the normal bladder and rectum tissue when the cancer is treated with ionizing radiation therapy or anti-neoplastic alkylating agents.

A key to the success of the present invention's approach to protecting normal cells from the deleterious effects of an anticancer alkylating agent or ionizing radiation is the recognition that in the case of primary lung cancer in the lung target organ, the delivery and expression of a transgene by inhalation would be expected to be 10 to 100 times greater in normal tissue than in poorly aerated cancer cells of that tissue. The greater delivery of a particular cancer therapy to tumor tissue, as compared with the delivery to normal tissue, is known as the therapeutic ratio. The therapeutic ratio determines the relative tumor killing as compared to normal tissue damage, as defined by an integral dose. The present invention exploits to advantage the poor aeration of the tumor tissue. For example, lung cancers are usually solid and poorly aerated. Also, the anatomic location of lung tumors in collapsed distal airways makes the tumor less accessible to the inhalation gene therapy, compared to the normal lung tissue. These conditions decrease the delivery of genes introduced by inhalation therapy to the lung cancer cells and increase the expression of radiotherapy or chemotherapy protective genes in normal cells, relative to the tumor cells.

In order to establish that the transgene is delivered and expressed more efficiently in normal tissue as compared to tumors of such tissue, a solid tumor is established in normal tissue of experimental animals, e.g., rats or mice, and expression of the transgene, relative to the normal tissue surrounding it, is assessed. A lower expression of the transgene in the transplanted tumor cells compared to the normal surrounding tissue illustrates the lower ratio of delivery of therapeutic genes to tumor cells than normal cells targeted for protection.

Compositions according to the present invention comprise a polynucleotide that encodes a protein that is transiently expressed in a subject when the subject is exposed to an agent that elicits production of a toxic species, such as a free radical, a superoxide anion, or a heavy metal cation, wherein the protein is capable of neutralizing or eliminating the toxic species; and a pharmaceutically acceptable vehicle for the polynucleotide. In this context a pharmaceutically acceptable vehicle can be a solid, liquid or gaseous material that can be used as a vehicle for administering a medicament because the material is inert or otherwise medically acceptable, as well as compatible with the active agent, in a particular context of administration. In addition to a suitable excipient, a pharmaceutically acceptable carrier can contain conventional additives like diluents, adjuvants, antioxidants, dispersing agents and emulsifiers, anti-foaming agents, flavor correctants, preservatives, solubilizing agents and colorants. More particularly, pharmaceutically acceptable vehicles are characterized by having physiologically acceptable pH and ionic strength. Sterile, buffered saline, particularly phosphate-buffered saline, is a preferred vehicle for compositions to be administered intravenously or parenterally.

Free Radical, Superoxide Anion and Heavy Metal Cation-Scavenging Proteins

Glutathione (GSH) detoxifies free-radicals. Cells generally synthesize GSH de novo from the constituent amino acids. γ-Glutamyltranspeptidase (γ-GTP) is a plasma membrane-associated ectoenzyme that catalyzes the transpeptidation of extracellular glutathione into amino acid intermediates, which are then transported across the cell membrane and used to resynthesize glutathione de novo. A cell's sensitivity to radiation is directly correlated with its ability to transpeptidate extracellular glutathione via γ-GTP. Cell lines with high γ-GTP activity are more resistant to the effects of radiation and are more capable of repairing damage induced by low doses of γ-irradiation than cell lines with low γ-GTP activity. See Examples 7 and 8. Tumor cells depleted of GSH have been shown to be more susceptible to ionizing irradiation and chemotherapeutic agents because GSH-dependent detoxification pathways are reduced. Louie et al., *Cancer Res.* 45: 2110 (1985).

Protection against superoxide radicals requires antioxidants, such as GSH, and the $O_2$-scavenging enzyme superoxide dismutase (SOD). SODs are metalloenzymes that are essential for dismutation of $O_2^-$ to $H_2O_2$ and $O_2$. There are three forms of SODs: copper-zinc (CuZnSOD), manganous (MnSOD) and iron (FeSOD). Although CuZn- SOD and FeSOD are made constituitively, MnSOD synthesis is inducible. Induction of MnSOD activity has been shown to follow X-irradiation of heart tissue. Oberley et al., *Arch. Biochem. Biophys.* 254: 69 (1987). Further, hematopoietic tumor cell lines transfected with MnSOD cDNA in vitro demonstrate increased resistance to radiation. Suresh et al., *Experimental Hematology* 21: 1828 (1993).

Metallothioneins are low molecular weight proteins consisting of a single polypeptide chain of 61 amino acid residues, of which 20 are cysteines that chelate cations. Induction of metallothionein has been shown to provide resistance to ionizing irradiation damage. Metallothionein protein protects cells from the toxic effects of heavy metal ions and is a powerful scavenger of radiation-induced OH-radicals in vitro. Cells lines that express high levels of MT are resistant to DNA damaging agents, such as cis-platinum and chlorambucil, and ionizing radiation. Andrews et al., *Cancer Chemother. Pharmacol.* 19: 149 (1987); Bakka et al., *Experientia* 38: 381 (1982); Matsubara et al., *Environ. Res.* 43:66 (1987). Metallothionein is capable of scavenging free radicals produced by electrophilic anticancer drugs and ionizing radiation in vitro. Endresen et al., *Cancer Res.* 43:2918 (1983); Thornalley et al., *Biochim., Biophys. Acta* 827:36 (1985). Importantly, induction of MT in mouse liver provides protection against lethal damage from high dose radiation. Matsubara et al., *Rad. Res.* 111: 267 (1987). Nonetheless, some cell lines transfected with the MT gene in vitro were as sensitive to ionizing radiation and bleomycin as non-transfected recipient cells. However, MT transfected cells were resistant to mitomycin, suggesting that MT protein protects some cells in vitro from monofunctional alkylating and crosslinking agents but not from free radicals. Lohrer et al., *Carcinogenesis* 10:2279 (1989).

Transient expression of genes administered in vivo is viewed in this art as a major technical limitation to gene therapy. See Mulligan, *Science* 260: 926 (1993). In sharp contrast, the method of the present invention views transient expression of the genes as highly desirable because protection of the normal tissue is needed only for the period of radiation therapy or chemotherapy; thereafter, rapid clearance of the gene product is desirable. Transient expression is desirable because the prolonged clinical effects of elevated MT, γ-GTP and/or MnSOD are unknown. Also, clearing of the transgene and its vector may be clinically desirable after chemotherapy or radiation therapy to provide for the next phase of a combined modality therapeutic approach. The methods of the present invention are designed to result in transient or nonintegrated expression of an exogenous gene in vivo; however, in the event that a limited amount of stable integration of the exogenously provided DNA also results, the method of the present invention remains functional in its ability to provide a protein capable of neutralizing or eliminating a toxic ionic species in vivo.

According to one aspect of the invention, transient expression is achieved by directed introduction of the genetic material encoding the desired proteins into cells or by use of a heterologous virus genome as a vector. Methods for delivering genes into mammalian cells to provide transient expression that can be utilized for gene therapy include: papovaviruses, adenovirus, vaccinia virus, herpesviruses, poxviruses, polio virus, sindbis and other RNA viruses, ligand-DNA conjugates, adenovirus-ligand-DNA conjugates, naked DNA, lipofection and receptor-mediated gene transfer. See, eg., Mulligan, supra. Coen in VIROLOGY, Fields et al. (eds.) Raven Press, Ltd., (New York, 1990); Ferkol et al., *FASEB* 7: 1081 (1993). Animal model studies have efficiently transferred genes using retroviruses (Friedmann, *Science* 244: 1275 (1989)), adenoviruses (Rosenfeld et al., *Science* 252: 431 (1991); Rosenfeld et al., *Cell* 68: 143 (1992)) and liposomes (Felgner et al., *Nature* 349: 351 (1991). According to an alternate aspect of the current invention, transient expression is achieved by virtue of controlling transcription from an inducible promoter. Such a promoter can be the erg1, induced by radiation (Hallan, D. E. et al., supra, and Datta, R. et al. supra). The vector containing the gene(s) of interest is a plasmid. Such a plasmid will occasionally integrate into the genome, and clonal cell lines containing the sequences of interest can be established. The introduction of the plasmid into the cells can be by a chemical method or by electroporation, as further described herein.

DNA can be introduced into animals by intratracheal, intravenous, intraperitoneal, intramuscular, intrarectal, intra-vesicle (i.e. intra-bladder), intraintestinal, intraoral, intraocular or intraarterial injections. Stribling et al., *Proc. Natl., Acad. Sci. USA* 89:11277 (1992). The lung is particularly accessible for in vivo gene therapy because of its direct access via the airway. Aerosol delivery of DNA using a plasmid/liposome complex is known to successfully transfect airway epithelial and alveolar lining cells in vivo and achieve high-level, lung-specific transgene expression in vivo. Stribling et al., supra and WO 93/12756. The bladder and rectum are also particularly accessible for in vivo gene therapy because of their direct access by either intra-vesicle infusion of the bladder or intrarectal instillation by local enema or by a suppository to reach the rectum.

According to the invention, direct introduction of nucleic acids into any human cells is achieved using several procedures. Nucleic acids can be co-precipitated with calcium phosphate. This form of DNA is taken up by cells more readily than naked nucleic acids. Graham et al., *Virology* 52: 456 (1973).

Introduction of genes into cells of intact animals is also achieved using receptor-mediated gene transfer, which employs ligand-DNA conjugates. Briefly, a chimeric gene containing the cDNA for human MT, γ-GTP or SOD, preferably MnSOD, is ligated to a promoter appropriate for the target tissue. The chimeric gene is then complexed to a carrier containing a ligand which will bind to the cell-specific or tissue-specific receptor present on the desired target tissue. For example, when the liver is the tissue targeted for gene therapeutic protection against free radicals, the DNA encoding the free radical scavenging protein is complexed to a synthetic neoglycoprotein that will target the complex to the asialoglycoprotein receptor on hepatocytes. An example of a carrier useful for receptor-mediated gene transfer to liver is a synthetic glycoprotein in which bovine serum albumin (BSA) is covalently bound to poly L-lysine using 1-ethyl-3-(3-dimethylaminopropyl) carbodiimide (EDC). Ferkol et al., supra. The entire structure is subsequently glycosylated using D-galactose.

To produce a neoglycoprotein conjugate for use in targeting DNA to liver, a reaction mixture that contains about 170 mM galactose, 4 mM poly (L-lysine), 160 mM BSA and 10 mM EDC (pH 7.5) can be incubated for 48 hours at 22° C. DNA is complexed to the neoglycoprotein carrier in a 360:1 molar ratio. The carrier-DNA complexes are dialyzed against 150 mM sodium chloride before transfection.

Expression of the functional protein after receptor-mediated transfection tends to be transient. Ferkol et al., supra. Cell specific receptors are well known to those of skill in the art, as are their ligands which can be used in complexes for receptor-mediated gene transfer. A variation of receptor-mediated gene transfer employs the coupling of monoclonal antibodies to liposome/plasmid complexes, thereby targeting the cells expressing the corresponding cell surface antigen. Maruyama et al., *Proc. Natl. Acad. Sci. USA* 87: 5744 (1990). Any tissue of the human body can be targeted for the gene therapy of the present invention using the disclosed methods. The criteria for a suitable target tissue is that it is susceptible to genetic modification of the present invention.

Another embodiment utilizes artificial lipid membranes (i.e., liposomes) to deliver DNA to cells. Procedures for introducing DNA into cells that employ lipid include: polyethylene glycol to mediate fusion of protoplast derived from plasmid-containing bacteria (Schaffner, *Proc. Natl. Acad. Sci. USA* 77: 2163 (1980); DNA-containing erythrocyte ghosts (Wiberg et al., *Nucleic Acids Res.* 11:7287 (1983); DNA-containing liposomes (Fraley et al., *Proc. Natl. Acad. Sci. USA* 76: 3348 (1979); plasmid/cationic liposome complexes (Stribling et al., supra; WO93/12756) and lipofection (Felgner et al., *Proc. Natl. Acad. Sci. USA* 84:7413 (1987). The gene therapy method of the present invention can employ any of the above procedures for introducing genetic material into cells in vivo.

Viruses provide an excellent way to introduce genes into mammalian cells because they are able to introduce multiple copies of the gene of interest into every cell in a culture, thus providing high efficiency transfection in vivo. Adenoviral vectors provide one useful means for delivering genes in vivo because adenoviruses can efficiently infect nondividing cells and can direct various cell types to express large amounts of gene products. Vector-mediated gene expression can be achieved in a variety of tissues by administration of a concentrated solution containing a desired adenoviral vector. Rosenfeld et al., *Science* 252: 431 (1991); Quantin et al., *Proc. Natl. Acad. Sci. USA* 89: 2581 (1992); Stratford-Perricaudet et al., *J. Clin. Invest.* 90: 626 (1992); Rosenfeld et al., *Cell* 68: 143 (1992); Stratford-Perricaudet et al., *Bone Marrow Transplant.* 9: 151 (1992); Jaffe et al., *Nat. Genet.* 1:374 (1992). Adenovirus vectors can be prepared using strategies well known to those of ordinary skill in the art. See Rosenfeld et al. *Science* 252:431 (1991) or Ghosh-Choudhoury et al., *Gene* 50: 161 (1986), the contents of which are incorporated by reference in their entirety.

When the method of the present invention is directed toward protecting normal lung tissue in a patient whose lung cancer is being treated with radiation therapy or chemotherapy, several approaches for delivering genes to the lungs can be used. See Mulligan, *Science* 260: 926 (1993) for a review of gene therapy. Such approaches include: retroviruses, adenoviruses (Rosenfeld et al., *Cell* (1992) supra; Rosenfeld et al., *Science* (1991) supra, adeno-associated viruses, and liposomes (WO93/12756; Stribling et al., supra; Brigham et al. *Am. J. Med. Sci.* 298: 278 (1989); Felgner et al., *Proc. Natl. Acad. Sci USA* 84: 7413 (1987). For transfection of pulmonary epithelium, the method of the present invention preferably utilizes adenoviral vectors, lipofection with liposomes or ligand-DNA conjugates.

The method of the present invention can be directed toward protecting normal bladder and rectal tissue in a patient whose prostate, bladder, cervical, ovarian or endometrial cancer is being treated with radiation therapy or chemotherapy. Several approaches for delivering genes to the bladder, and rectum can be used. For example, intra-vesicle and intra-rectal instillation of liposome vectors containing DNA encoding MT, MnSOD and/or γ-GTP.

Lipofection

In one embodiment of the invention, DNA is transferred into cells by lipofection. The technique employs a liposome formulation of cationic lipid to transfect nucleic acids into cells. The lipid-nucleic acid complex fuses with plasma membranes and transfers the nucleic acid into the cells efficiently, and the DNA is expressed. Lipofection is five to one hundred times more efficient in introducing DNA into cells than calcium phosphate or DEAE-dextran transfection methods. Chang et al., *Focus* 10: 66 (1988). Liposome preparations can be prepared as described in the art or purchased from commercially available sources, such as GIBCO BRL's lipofectin (GIBCO BRL, Life Technologies, Inc., P.O. Box 9418, Gaithersburg, Md. 20898). Felgner et al., (1987) supra; Schreier, *J. of Liposome Res.* 2: 145 (1992); Chang et al., (1988) supra.

Transient transfection employing lipofection is measured 24 to 72 hours after transfection by assays that measure gene expression of the transfected gene(s). Commonly used assays monitor enzyme activities of chloramphenicol acetyltransferase (CAT), LAC-Z, β-galactosidase, luciferase, or human growth hormone that can be contained in the constructs. Using lipofection, human small cell lung cancer cells have been transiently transfected. Chang et al. supra. Lipofection of DNA encoding MT, CuZnSOD, FeSOD, MnSOD and γ-GTP encoding DNA to any target tissue can be performed using lipofection techniques well known to those of skill in the art, such as those disclosed in Example 5.

Liposome complexes are particularly useful in aerosol delivery of DNA to the lungs, where aerosolized plasmid/liposome complexes can mediate DNA delivery and expression throughout the airways and alveoli. Stribling et al., (1992) supra and WO 93/12756. Cationic liposomes can be used as one preferred component of the plasmid/liposome complex for targeting DNA to cells of the lungs. Several factors are important in both (a) the ability of a particular lipid carrier-nucleic acid complex to transform lung cells following aerosolized delivery of a solution containing the lipid carrier-nucleic acid construct and (b) the achievement of high level expression in the lung. These factors include: (1) preparing a solution that does not form macroaggregates and wherein the nucleic acid is not sheared into fragments prior to or during nebulization and (2) preparing both lipid carriers and expression constructs that provide for predictable transformation of host lung cells following aerosolization of the lipid carrier-nucleic acid complex and administration to the host animal.

One preferred preparation of a cationic lipid preparation is composed of 1:1 DOTMA or DDAB/DOPE (i.e., 1:1 of N-[1-(2,3-dioleyloxy)propyl]-N,N,N-triethylammonium (DOTMA) or dimethyldioctadecyl-ammoniumbromide (DDAB) and cholesterol and dioleoyl phosphatidylethanolamine (DOPE). To produce 1:1 DOTMA/DOPE cationic liposomes, stock solutions of lipids are dissolved in chloroform and stored under argon at −20° C. Lipids are mixed in round bottomed flasks and evaporated to dryness on a rotary evaporator under reduced pressure. Final lipid concentrations of 10 mM each are made by adding double-distilled water. The resulting mixture is sonicated to produce a suspension of liposomes.

Plasmid is complexed to DOTMA/DOPE liposomes as follows. Plasmid DNA and DOTMA/DOPE liposomes are diluted separately in water prior to being mixed. The volume of water may range between 1 and 20 ml, preferably about 8 ml. The composition of the liposome-DNA complex may range from about 4:1 to about 1:10 micrograms DNA to nanomoles of cationic lipid, preferably from about 1:1 to 1:2 micrograms DNA to nanomoles of cationic lipid. A solution containing the liposome-DNA complex is aerosolized using a nebulizer. Typical solutions containing the liposome-DNA complex can be sterile water or a pharmaceutically acceptable carrier or diluent. Subjects are exposed to an air flow rate that generates an aerosol. Approximately 90 minutes are required to aerosolize typical volume dosages.

Adenovirus

In another embodiment of the invention, cDNA is transferred into non-proliferating epithelial cells utilizes a replication-deficient recombinant adenovirus that contains an active promoter and the cDNA to be transferred. The adenovirus is tropic for respiratory epithelium and capable of transferring recombinant genes into non-proliferating cells. A recombinant adenovirus of the present invention can be constructed so as to transfer and express, in respiratory epithelium, the DNA encoding either gamma glutamyl transpeptidase, manganese superoxide dismutase, metallothionein, a combination of DNA sequences encoding any two of these proteins, or a combination of DNA sequences encoding all three of these proteins.

A vector is tested for its ability to direct the biosynthesis of functional protein, by in vitro studies in cultured cells using the specific MT, γ-GTP, SOD or MnSOD functional assays disclosed herein.

DNA Encoding γ-GTP, MnSOD and MT

A DNA sequence encoding the entire superoxide dismutase, preferably MnSOD, coding region is isolated or synthesized by methods well known to the art based on the MnSOD sequences reported by Oursler et al., *J. Cell. Biochem.* 46: 219 (1991) or Beck et al., *Nucl. Acids. Res.* 15: 9076 (1987), or the SOD sequences reported by U.S. Pat. No. 4,751,180; Lieman-Hurwitz et al., *Proc. Natl. Acad. Sci. USA* 79: 2808 (1982); U.S. Pat. No. 4,742,004; Xiang et al., *Nucleic Acids Res.* 15: 7654 (1987) or Sherman et al., *Proc. Natl. Acad. Sci. USA* 80: 5465 (1983), the contents of each of which are incorporated by reference in their entirety. Alternatively, these sequences are prepared by the polymerase chain reaction by methods well known to those of skill in the art. See, e.g., Wong et al., *Cell* 58: 923 (1989).

DNA sequences encoding various species and isoforms of metallothionein can be isolated or synthesized by methods well known to the art based on the sequences reported for human MT by [Yamazaki et al., *Biochem Int.* 28:451 (1992); Soumillion et al., *Eur. J. Biochem.* 209: 999 (1992); Karin et al., *Proc. Natl. Acad. Sci. USA* 80:4040 (1983); Paliwal et al., *Neurochem. Int.* 17: 441 (1990); Schmidt et al., *J. Biol. Chem* 260: 7731 (1985); Richards et al., *Cell* 37: 263 (1984); Karin et al., *Nature* 299: 797 (1982); Hyland et al., *Nucleic Acids Res.* 15: 1350 (1987);, sheep and mouse [Peterson et al., *Eur. J. Biochem.* 160:579 (1986)], fish [(Lee et al., *Korean Biochem J.* 25: 48 (1992); Bonham et al., *DNA* 6:519 (1987)] and insect [Lastowski-Perry et al., *J. Biol. Chem.* 260:1527 (1985)], the contents of each of which are incorporated by reference in their entirety. Preferably, the human metallothionein sequences disclosed by either Yamazaki et al., (1992) supra, or Soumillion et al., (1992) supra are used in the method of the present invention.

DNA encoding γ-GTP can be provided for use in the present invention by isolating or synthesizing such a sequence by methods well known to the art based on the sequences reported by any of Altman et al., *Biochemistry* 32: 3822 (1993); Ishiye et al., *Biotech. Progr.* 9: 323 (1993); Ishiye et al, *FEMS Mirobiol. Lett.* 97: 235 (1992); or Angele et al., *Clin. Chem.* 37: 662 (1991), the contents of each of which are hereby incorporated by reference. DNA encoding MT, SOD, MnSOD, or γ-GTP can be provided for use in the present invention by methods well known to those of skill in the art, such as (1) oligonucleotide synthesis of the desired DNA sequences based on the sequences disclosed in the above recited references; (2) isolation of the desired DNA sequences from the plasmids disclosed in the above references or from plasmids available from American Type Culture Collection (ATCC) (12301 Parklawn Drive, Rockville, Md. 20852) such as: [a] ATCC 57117—pHM6 containing the human metallothionein 2 pseudogene 1; [b] ATCC 57152, 57153—bMT-IIA containing the human metallothionein 2 gene; [c] ATCC 20745—pYAS11 containing cDNA encoding human superoxide dismutase 1; [d] ATCC 20796—pYLUIGF2-14 containing DNA encoding human superoxide dismutase 1; [e] ATCC 39786—pSOD alpha 2 containing DNA encoding human superoxide dismutase 1; [f] ATCC 59946, 59947—phMnSOD4 containing DNA encoding human superoxide dismutase 2; [g] ATCC 61646, 61647 containing cDNA encoding human superoxide dismutase 1; [h] ATCC 86406—IB881 containing cDNA encoding human superoxide dismutase or (3) polymerase chain reaction amplification of the desired DNA sequences from the DNA libraries disclosed in the above references using primers based on the sequences disclosed in the recited references.

Recombinant Adenoviruses

To specifically transfer DNA capable of expressing γ-GTP, MT, SOD and/or MnSOD in a desired/particular human target tissue in vivo, replication-deficient recombinant adenoviruses can be used.

For example, Ad.CMV-lacZ (containing cytomegalovirus) and Ad.CB-MnSOD viruses, which are based on adenovirus type 5 (Ad5) and produced by homologous recombination in transformed primary human embryonal kidney cell line 293 (ATCC Catalogue Number CRL1573) can be used in the method of the present invention. Graham et al., METHODS IN MOLECULAR BIOLOGY (Murray, Humana, 1991).

To construct the recombinant adenovirus of the present invention, approaches well known to those of ordinary skill in the art can be utilized. For example, the recombinant adenovirus of the present invention is constructed from an adenovirus type 5 (Ad 5) deletion mutant, such as Ad-dl324 (Thimmappaya et al., *Cell* 31:543 (1982)) and a plasmid containing the Ad5 5' inverted terminal repeat, origin of replication, encapsidation signal, E1a enhancer, the major late promoter, the tripartite leader sequence cDNA and the DNA sequence encoding the entire protein sequence of human MT, γGTP or MnSOD and the SV40 early polyadenylation signal. The recombinant vectors Ad-MT, Ad-γ-GTP, and Ad-MnSOD are constructed by deleting the majority of the E3 region and 2.6 mu from the left end of Ad5 and adding to the left end the MT, γ-GTP or MnSOD expression cassettes, which contain the regulatory sequences and the recombinant MT, γ-GTP or MnSOD encoding DNA. The left end of the viral genome, including the E1a and the majority of the E1b region is deleted and replaced by the MT or γ-GTP or MnSOD expression cassette containing the essential viral cis-acting elements, including the inverted terminal repeat, an origin of replication, the encapsidation signal, the E1a enhancer and no E1a structural gene. Preferably, the E1a enhancer is followed by the adenovirus type 2 major late promoter and cDNA encoding the MT, γGTP or MnSOD. The constructed recombinant adenovirus is then replicated in a permissive cell line that contains a functional E1a gene to provide a transacting E1a protein, such as the 293 human kidney cell line. Thereafter, high titer, infectious recombinant adenoviral stocks are prepared.

A second way to produce the recombinant adenoviral vector of the present invention is to coprecipitate a linearized plasmid containing the desired cDNA encoding MT, γ-GTP or MnSOD with the large fragment of compatibly cut Ad-dl324 DNA using the calcium-phosphate precipitation method. Graham et al., *Virology* 52:456 (1973); Wigler et al., *Cell* 14:725 (1978). The co-precipitated DNAs are then cotransfected into 293 cells to allow homologous recombination to occur. Recombinant adenovirus DNA is tranfected into 293 cells (Graham et al., *J. Gen. Virol.* 35: 59 (1977); Graham et al., *Virology* (1973), supra) where it is replicated, encapsidated into an infectious virus and isolated by plaque purification. Individual plaques are amplified by propagation in 293 cells and viral DNA is extracted. Hirt, *J. Mol. Biol.* 26: 365 (1967).

Recombinant adenovirus plaques containing the human gamma glutamyl transpeptidase, manganese superoxide dismutase and metallothionein protein cDNA (Ad-γGTP; Ad-MnSOD, and Ad-MT respectively) are then identified by restriction cleavage, Southern analysis and/or Northern analysis using the appropriate DNA probes. Control virus having a deletion of the E1a region and not containing the DNA of interest will not demonstrate detectable γ-GTP, MnSOD or MT transcripts in a Northern analysis whereas constructs containing the DNA of interest will demonstrate a detectable γ-GTP, MnSOD or MT transcript.

Each of Ad-γGTP, Ad-MnSOD, and Ad-MT vectors are propagated in 293 cells and recovered 36 hours after infection by several cycles of freeze/thawing. All viral preparations are purified by $CaCl_2$ density centrifugation, dialyzed and stored in virus dialysis buffer (10 mM Tris-HCl, pH 7.4, 1 mM $MgCl_2$) at 4° C. for immediate use, or frozen at −70° C. with the addition of 10% glycerol. The titer of the viral stock is determined by plaque assays using 293 cells. Any tissue of the human body can be targeted for the gene therapy of the present invention using the adenoviral vectors described above. These vectors can be introduced by intratracheal, intravenous, intraperitoneal, intramuscular, intrarectal, intravesicle, intraintestinal, intraoral, intraocular or intraarterial injections.

For evaluation of MT, γ-GTP or MnSOD mRNA, or protein synthesis or the evaluation of functional protein, the recombinant vector is used to infect either 293 cells or rat respiratory epithelial cells. To obtain rat respiratory epithelial cells, rats are sacrificed, the lungs and trachea are isolated. Cells are obtained by cytologic brush (Rosenfeld et al., supra (1991) plated, and infected with $2\times10^7$ plaque forming units (PFU) of Ad-MT, Ad-γ-GTP, or Ad-MnSOD in media, or, as a control, exposed to only media.

According to the present invention, conditions are established for achieving recombinant gene expression in a majority of the cells of the target organ to be protected in vivo. For example, to achieve recombinant gene expression in the lung, a significant fraction of airway epithelial cells from the main bronchi down to the alveolar epithelial cells should be transfected with the construct. It may not be necessary to achieve greater than 50% transgene expression or even greater than 10% transgene expression if cell-to-cell protection is involved in the transfected organ. For example, one transgene expressing lung epithelial cell may be able to protect ten non-transfected cells in a local niche by cell-to-cell transfer of intermediates (eg., one nucleotide or one nucleoside) involved in the cellular repair cascade.

Animal Studies of Transfection In Vivo

The dosages of the pharmaceutical compositions administered according to this invention are generally known in the art. Generally, the preparations of this invention are dispensed in dosage unit form comprising between $10^6$ and $10^{14}$ PFU/ml of viral vector in a pharmaceutically acceptable carrier per unit dosage, preferably about $10^{10}$ to $5\times10^{13}$ PFU/ml of the replication-deficient adenovirus Ad-γ-GTP, Ad-MnSOD and/or Ad-MT. The desired pfu are contained in a total volume of between 0.3 and 2.0 ml of phosphate buffered saline (PBS) and administered by techniques known to one skilled in the art. DNA may been introduced into animals by intratracheal, intravenous, intraperitoneal, intramuscular, intravesicle, intraintestinal, intrarectal, intraoral, intraocular or intraarterial injections. For introduction into the lung, DNA can be introduced by instillation through a tube, infusion, inhalation into the trachea or injection into the trachea. For introduction into the bladder, the vector can be instilled into the bladder by intravesicle infusion. For introduction into the rectum, the vector can be instilled using a local enema.

Alternatively, inhalation therapy may be applied using a liposome aerosol dispersion containing cDNA for one of the three genes γ-GTP, MnSOD or MT or a mixture of all three genes. The dosage of liposome-DNA complex may range from about 5–50 mg plasmid per 5 to 100 μmoles of liposomes, preferably about 12 mg plasmid per 24 μmoles liposome. Preferably, DOTMA/DOPE Liposomes are used in the plasmid/liposome complex for aerosol gene delivery.

When a ligand-DNA complex is utilized to deliver the desired gene to the target cells, the ligand conjugate is complexed to plasmid DNA using a molar ratio of carrier to DNA of between approximately 10:1 and 500:1, preferably between 300:1 and 500:1. For example, when a synthetic neoglycoprotein carrier is complexed to a chimeric gene for targeting to the liver, the preferred molar ratio of carrier to DNA is approximately 360:1.

Expression of MT, γ-GTP and MnSOD

One day and serial time points after transfection, expression of recombinant MT, γ-GTP or MnSOD mRNA transcripts is evaluated by in situ hybridization using $^{35}$S-labeled sense and antisense RNA probes prepared in pGEM-3Z (Promega). Harper, *Proc. Natl. Acad. Sci. USA* 83: 772 (1986). After hybridization, the cells are evaluated by autoradiography and the cells are counterstained with hematoxylin and eosin.

Expression of MT, γ-GTP or MnSOD protein is evaluated by either immunoprecipitation or Western Blotting. For immunoprecipitation, the transfectants are labelled with $^{35}$S-methionine (500 μCi/ml for 24 hours at 37° C.) and cell supernatants are evaluated by immunoprecipitation with antibodies specific for the respective protein (i.e. MT, γ-GTP, or MnSOD). Antibodies specific for metallothionein can be obtained by the methods disclosed in each of Garvey, *Meth. Enzym.* 205: 141 (1991); Mesna, et al., *Comp. Biochem. and Phys.* 99: 181 (1991); Schmidt, et al., *J. Biol. Chem.* 260: 7731 (1985); or Tohyama et al., *Biochem Biophys. Res. Commun.* 84: 907 (1978), the contents of each are hereby incorporated by reference. Antibodies specific for MnSOD can be obtained by the method disclosed in either McCormick, et al., *Carcinogenesis* 12: 977 (1991) or St. Clair et al., *Free Radical Res. Commun.* 12: 771 (1991), the contents of each are hereby incorporated by reference. Antibodies specific for gamma glutamyl transpeptidase can be obtained by the methods disclosed in each of Ishiye et al., *Biotech. Progr.* (1993) supra; Ishiye et al., *FEMS Microbiol. Lett.* (1992) supra; or Angele et al., *Clin. Chem.* (1991) supra, the contents of each are hereby incorporated by reference. Alternatively, the expression of a linked reporter gene, such as LAC-Z, may be used to quantitate the number of cells expressing the transfected construct.

Analysis of Recombinant Gene Expression mRNA transcripts are evaluated in lung RNA (prepared as above) after conversion to cDNA, PCR amplification and Southern hybridization analysis. Rosenfeld et al., supra. To ensure that adenovirus driven transcripts are specifically evaluated and that the 5' and 3' portion of mRNA transcripts are present, two separate primer pairs are used: a 5' primer pair to detect the 5' end of recombinant adenovirus construct mRNA transcripts and a human MT, MnSOD or γ-GTP-specific antisense primer, and a 3' primer pair to evaluate the 3' end of the recombinant Adenovirus mRNA transcript and an SV40 viral-specific primer in the SV40 early mRNA polyadenylation signal sequence. Fiers et al., Nature 273: 113 (1978). Each RNA sample is used as a PCR template in parallel without conversion to cDNA, to eliminate the possibility that amplification of potentially contaminating viral DNA occurred.

PCR amplification products are evaluated by agarose gel electrophoresis followed by Southern hybridization using $^{32}$P-labeled human γ-GTP, MnSOD or MT cDNA probes.

Northern analysis of lung RNA from animals infected with the recombinant adenovirus will show Ad-MT, Ad-MnSOD or Ad-γ-GTP directed human mRNA transcripts of a size similar to that directed by these constructed in cultured cells, as compared to RNA from uninfected animals. Levels of a constituitively expressed protein, such as Beta-actin or glyceraldehyde-3phosphate dehydrogenase transcripts serve as a positive control and are normally similar for both infected and uninfected tissue samples.

Immunohistochemical Detection of the Human Gamma Glutamyl Transpeptidase, Manganese Superoxide Dismutase and Metallothionein After In Vivo Infection Human gamma glutamyl transpeptidase, manganese superoxide dismutase and metallothionein are evaluated in cytocentrifuge preparations of human lung epithelial lavage samples or lung biopsy samples taken 2 days, 7 days, 2 weeks, 4 week and 6 weeks after in vivo infection with Ad-MT, Ad-MnSOD or Ad-γ-GTP. The alkaline phosphatase monoclonal anti-alkaline phosphatase method is used with antibodies specific for human gamma glutamyl transpeptidase, manganese superoxide dismutase and metallothionein antibody. Cordell et al., *J. Histol. Cytochem.* 32: 219 (1984).

Evaluation of Functional Activity of Expressed Recombinant Protein

The in vitro or in vivo expressed human gamma glutamyl transpeptidase, manganese superoxide dismutase and metallothionein are each tested for their functional activity.

Assay of Functional MT

Analysis of cytoplasmic metallothionein protein is performed using cells transformed in vitro, or cells obtained from biopsy or pulmonary lavage. Cells are pelleted and resuspended in 250 mM Tris-HCl (pH 7.6) and frozen/thawed three times at −70° C. and +37° C., respectively. After centrifugation to pellet cellular particulate fraction in a centrifuge, the protein concentration of the supernatant is determined. Protein (0.4 mg) is incubated with 100,000 counts per minute (CPM) of $^{109}$Cd$^{2+}$ overnight at 4° C. The proteins are separated on a Sephadex G100 column eluted with Bell's buffer (20 mM Tris-HCl, 50 mM NaCl, pH 8.6).

From each sample, 120 fractions of 3 ml are collected and their γ-radioactivity is determined. In parental cells lines, the gamma activity is associated with high molecular weight protein. In the protein extracts from transfectants expressing functional MT, the $^{109}$Cd is mainly associated with a highly abundant protein of the molecular weight of MT, which is about 6,000 daltons.

Assay of Functional MnSOD

MnSOD constitutes a minor fraction of the total pulmonary SOD activity and require a sensitive assay for tissues expressing low SOD activities. Tsan, *Proc. Soc. Exp. Biol. Med.* 203: 286 (1993). Mn-SOD activity can be assayed in tissues with low SOD activity using the Oberley assay. Oberley et al., *Meth. Enzym.* 105: 457 (1984) and Oberley et al., in HANDBOOK OF METHODS FOR OXYGEN RADICAL RESEARCH, R. Greenwald (ed.) (Boca Raton, Fla.; CRC Press 1985), the entire contents of each reference are incorporated herein by reference. Briefly, a competitive inhibition assay is performed that uses xanthine—xanthine oxidase generated $O_2$ to reduce nitroblue tetrazolium (NBT) at a constant rate. The rate of NBT reduction is monitored spectrophotometrically at 560 nm. One unit of SOD activity is defined as the amount of protein that inhibits the NBT reduction to 50% of its maximum reduction rate. To differentiate between CuZnSOD and MnSOD activities, the assay inhibits CuZnSOD by using 5 mM sodium cyanide. Enzymatic activity is expressed in Units per mg of protein.

Assay of Functional γ-GTP Activity

γ-GTP activity is measured in cell free extracts by a modification of chromogenic method. Tate et al., *Proc. Natl. Acad. Sci. USA* 75: 4806 (1978) and Griffith, O. W., "Mechanism of action, metabolism, and toxicity of buthionine sulfoximine and its higher homologs, potent inhibitors of glutathione synthesis", *J. Biol. Chem.* 257:13704–13712 (1982). Cell lysate is added to a reaction mixture containing 2 mM L-γ-glutamyl-p-nitroanilide, 20 mM glycylglycine, 75 mM NaCl and 200μ Tris-HCl buffer pH 7.5. The reaction mixture is incubated at room temperature and the absorbance measured spectrophometrically at 410 nm. In the presence of enzyme, L-γ-glutamyl-p-nitroanilide donates a glutamyl group to glycylglycine forming the conversion products p-nitroaniline and γ-glutamylglycylglycine. The activity is expressed as nanomoles of p-nitroaniline released per $10^6$ cells per hour. A molar extinction coefficient of 10.4 mM$^{-1}$cm$^{-1}$ is used for absorbance conversions. Allen et al., *Chem. Pathol. Pharmacol.* 27: 175 (1980).

The contents of all documents referenced herein are hereby incorporated in their entirety. Without further elaboration, it is believed that one skilled in the art can, using the preceding description, utilize the present invention to its fullest extent.

In carrying out the assay of this invention, the quantities of materials utilized are not in themselves critical and can be varied within the scope and spirit of the invention. Without further elaboration, it is believed that one skilled in the art can, using the preceding description, utilize the present invention to its fullest extent. The following examples are merely illustrative of preferred embodiments and not intended to be limitative of the remainder of the disclosure in any way whatsoever.

EXAMPLE 1

Figure 1B:
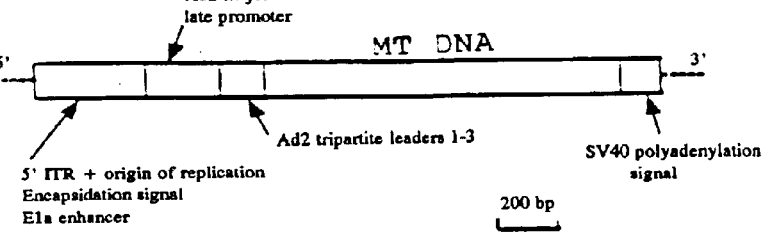

Construction of the Recombinant Adenoviral Vector Ad-MT and Expression of Recombinant MT from Lung Epithelium In Vivo The adenovirus major late promoter is linked to a recombinant human MT gene (Yamazaki et al., supra; Soumillion et al., supra) and is incorporated into a replication-deficient recombinant. Straus in THE ADENOVIRUSES, Ginsberg (ed.) (Plenum Press, New York 1984); Gilardi et al., *FEBS Lett.* 267: 60 (1990). The vector has a deletion of part of the E3 region and part of the viral E1a coding sequence, yet contains an insert of an MT expression cassette (FIGS. 1A and 1B). Ad-MT is constructed by deleting the majority of the E3 region and a portion of the left end of Ad5 and adding to the left end of the MT expression cassette from a plasmid containing the nucleic acid sequence encoding MT. Once the expression cassette is packaged into an infectious, replication-deficient virus, Ad-MT is capable of directing the synthesis of human MT in 293, CHO and HeLa cell lines. Gilardi et al., supra.

Ad-MT is used to transfect various target tissue. For example Ad-MT directs the synthesis of MT in rat lung in vivo. Human MT transcripts are observed in the transfected lungs two days after intratracheal instillation of Ad-MT, but not in lungs that received only buffer or the Ad5 E1a-deletion mutant not containing the MT gene. Lung biopsies removed from infected animals at various times after infection are biosynthetically labelled. Protein from such samples are immunoprecipitated with anti-MT antibody. SDS-PAGE and autoradiography reveal de novo expression of about a 6,000 dalton human MT.

The expression of functional MT is assessed using the MT functional assay. Protein, 0.4 mg, from the biopsied lung tissue is incubated in 100,000 CPM of $^{109}Cd^{2+}$ overnight at 4° C. The proteins are separated on a Sephadex G100 column eluted with Bell's buffer (20 mM Tris-HCl, 50 mM NaCl, pH 8.6). From each sample, 120 fractions of 3 ml are collected and their radioactivity is determined. In the tissues not receiving the MT gene, the gamma activity is associated with high molecular weight protein. In the protein extracts from transfectant expressing functional MT, the $^{109}Cd$ is mainly associated with a highly abundant protein of about the 6,000 dalton molecular weight of MT.

Figure 3A:
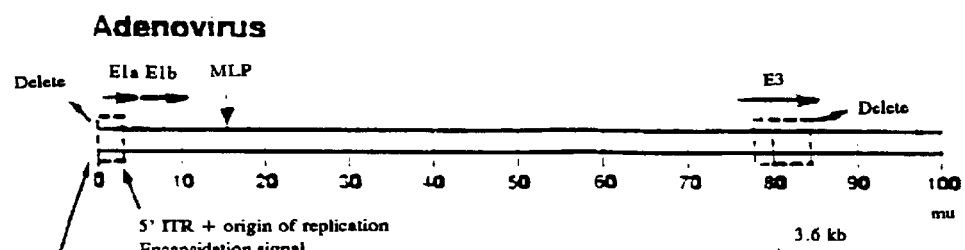
FIGS. 3A and 3B are schematic drawings of the construction of a manganese superoxide dismutase recombinant adenovirus vector (Ad-MnSOD).
Figure 3B:
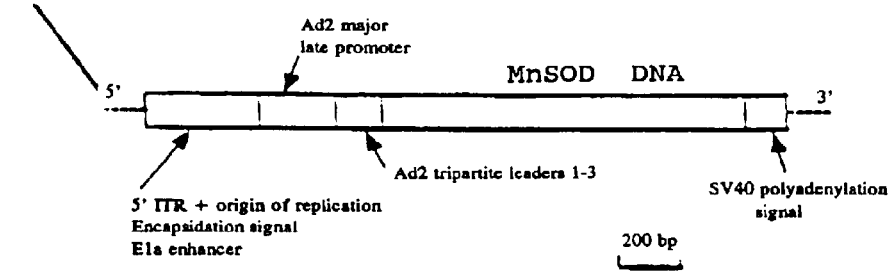

EXAMPLE 2
Construction of the Recombinant Adenoviral Vector Ad-MnSOD and Expression of Recombinant MnSOD from Lung Epithelium In Vivo The adenovirus major late promoter is linked to a recombinant human MnSOD gene (Beck et al., Nucl. Acids. Res. 15: 9076 (1987)) and is incorporated into a replication-deficient recombinant. Straus, supra; Gilardi et al., supra. The vector has a deletion of part of the E3 region and part of the viral E1a coding sequence, yet contains an insert of an MnSOD expression cassette. Ad-MnSOD is constructed by deleting the majority of the E3 region and a portion of the left end of Ad5 and adding to the left end of the MnSOD expression cassette from a plasmid containing a nucleic acid sequence encoding MnSOD (FIGS. 3A and 3B). Once the expression cassette is packaged into an infectious, replication-deficient virus, Ad-MnSOD is capable of directing the synthesis of human MnSOD in 293, CHO and HeLa cell lines. Gilardi et al., supra.

Ad-MnSOD is used to transfect various target tissue. For example Ad-MnSOD directs the synthesis of MnSOD in rat lung in vivo. Human MnSOD transcripts are observed in the transfected lungs two days after intratracheal instillation of Ad-MnSOD, but not in lungs that received only buffer or the Ad5 E1a-deletion mutant not containing the MnSOD encoding DNA. Lung biopsies removed from infected animals at various times after infection are biosynthetically labelled. Protein from such samples are immunoprecipitated with anti-MnSOD antibody. SDS-PAGE and autoradiography reveal de novo expression of human MnSOD of about 16,000 to 19,000.

The expression of functional MnSOD is assessed using the MnSOD functional assay. Tsan (1993) supra; Oberley et al., Meth. Enzym. 105: 457 (1984); Oberley et al., in HANDBOOK OF METHODS FOR OXYGEN RADICAL RESEARCH, R. Greenwald (ed.) (Boca Raton, Fla.; CRC Press 1985), the entire contents of each reference are incorporated herein by reference. A competitive inhibition assay is performed that uses xanthine—xanthine oxidase generated $O_2-$ to reduce nitroblue tetrazolium (NBT) at a constant rate. The rate of NBT reduction is monitored spectrophotometrically at 560 nm. To differentiate between CuZnSOD and MnSOD activities, the assay inhibits CuZnSOD by using 5 mM sodium cyanide. Enzymatic activity is expressed in Units per mg of protein.

Figure 2A:
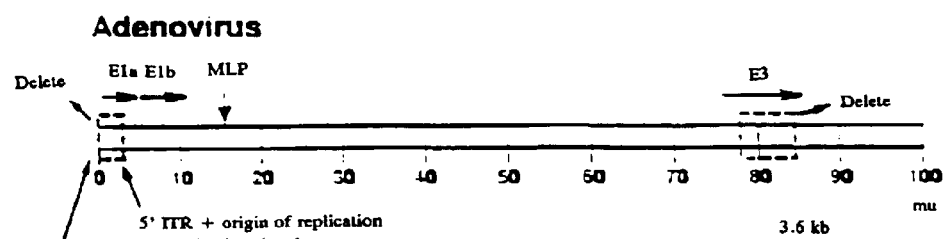
FIGS. 2A and 2B are schematic drawings of the construction of a gamma-glutamyltranspeptidase recombinant adenovirus vector (Ad-γ-GTP).
Figure 2B:
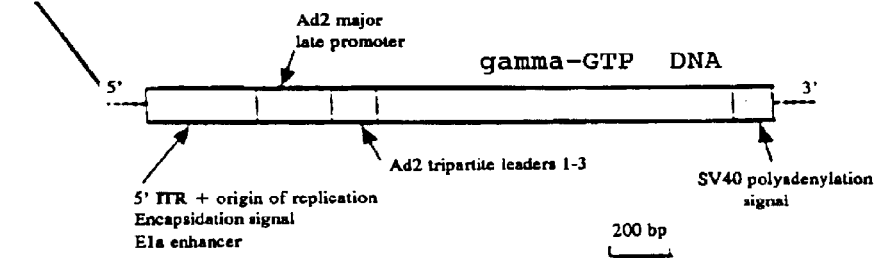

EXAMPLE 3
Construction of the Recombinant Adenoviral Vector Ad-γ-GTP and Expression of Recombinant γ-GTP from Lung Epithelium In Vivo The adenovirus major late promoter is linked to a recombinant human γ-GTP gene (Altman et al., Biochemistry 32: 3822 (1993) and incorporated into a replication-deficient recombinant. Straus, supra; Gilardi et al., supra. The vector has a deletion of part of the E3 region and part of the viral E1a coding sequence, yet contains an insert of an γ-GTP expression cassette (FIGS. 2A and 2B). Ad-γ-GTP is constructed by deleting the majority of the E3 region and a portion of the left end of Ad5 and adding the left end of the γ-GTP expression cassette from a plasmid containing the nucleic acid sequence encoding γ-GTP. Once the expression cassette is packaged into an infectious, replication-deficient virus, Ad-γ-GTP is capable of directing the synthesis of human 1-GTP in 293, CHO and HeLa cell lines. Gilardi et al., supra.

Ad-γ-GTP is used to transfect various target tissues. For example Ad-γ-GTP directs the synthesis of γ-GTP in rat lung in vivo. Human γ-GTP transcripts are observed in the transfected lungs two days after intratracheal instillation of Ad-γ-GTP, but not in lungs that received only buffer or the Ad5 E1a-deletion mutant not containing the γ-GTP gene. Lung biopsies removed from infected animals at various times after infection are biosynthetically labelled. Protein from such samples are immunoprecipitated with anti-γ-GTP antibody. SDS-PAGE and autoradiography reveal de novo expression of about a 62,000 molecular weight human γ-GTP.

The expression of functional γ-GTP is assessed using the γ-GTP functional assay. γ-GTP activity is measured in cell free extracts by a modification of chromogenic method. Tate et al. Proc. Natl. Acad. Sci. USA 75: 4806 (1978). Cell lysate is added to a reaction mixture containing 2 mM L-γ-glutamyl-p-nitroanilide, 20 mM glycylglycine, 75 mM NaCl and 200μ Tris-HCl buffer pH 7.5. The reaction mixture is incubated at room temperature and the absorbance measured spectrophometrically at 410 nm. In the presence of enzyme, L-γ-glutamyl-p-nitroanilide donates a glutamyl group to glycylglycine forming the conversion products p-nitroaniline and γ-glutamylglycylglycine. The activity is expressed as nanomoles of p-nitroaniline released per $10^6$ cells per hour. A molar extinction coefficient of 10.4 $mM^{-1}cm^{-1}$ is used for absorbance conversions. Allen et al., supra.

EXAMPLE 4
Expression of a Combination of Recombinant MT, MnSOD and γ-GTP from Lung Epithelium In Vivo A combination of Ad-MT, Ad-MnSOD and Ad-γ-GTP is used to transfect various target tissues. For example the following combinations of: (a) Ad-γ-GTP and Ad-MT, or (b) Ad-γ-GTP and Ad-MnSOD, or (c) Ad-MT and Ad-MnSOD or (d) each of Ad-MT and Ad-MnSOD and Ad-γ-GTP are cotransfected in rat lung in vivo to direct the synthesis of the respective recombinant proteins. For example, Sprague-Dawley or Cotton rats are anesthetized and 300 μl of $10^8$ PFU of Ad-MT, Ad-MnSOD and/or Ad-γ-GTP/ml PBS is instilled into their trachea. Alternatively, lipid carrier-nucleic acid complexes (WO93/1275; Stribling et al., supra) or a ligand/DNA complex containing MT, MnSOD and/or γ-GTP encoding DNA can be used to deliver the desired DNA to the lung via aerosol.

The assays discussed in Examples 1 through 3 are employed to assess the expression of recombinant and functional protein. For example, at various times after infection, the lungs are minced, incubated in methionine-free media for 1 hour at 37° C. and then incubated for 24 hours in $^{35}$S-methionine containing medium. The supernatant is then evaluated by immunoprecipitation with the respective MT, MnSOD, or γ-GTP specific antibodies, followed by SDS-polyacrylamide gels, and autoradiography.

EXAMPLE 5
Expression of Recombinant MT, MnSOD and/or 1-GTP from Lung Epithelium Using a Liposome Vector Lipid carrier-nucleic acid complexes can be prepared by methods well known in the art, such as those disclosed by Debs et al., WO93/12756 or Stribling et al., supra, the entire contents of which is incorporated by reference herein. Alternatively liposomes for lipofection can be produced as follows or purchased from GIBCO BRL. To prepare liposomes for lipofection, 20 mg of egg phosphatrolycholine is rotary evaporated with a vacuum drier from a chloroform solution to form a thin film on the walls of a 5 ml round-bottomed flask for 1 hour. The dried thin film lipid is suspended in 0.5 ml phosphate buffered saline (PBS) pH 7.4 on a vortex mixer and then sonicated.

To entrap DNA in the sonicated liposome suspension, 0.5 ml of DNA solution is extensively vortexed with the sonicated suspension for 1 minute followed by three cycles of freezing and thawing. DNA entrapped liposomes are separated from the non-entrapped DNA by gel filtration on a Sepharose 4B column diluted with PBS.

The amount of liposomes (30–40 µg) and the amount of DNA (1 to 5 µg) can be optimized for each cell type based on a dose response curve to determine cell toxicity. Felgner et al., (1989) supra. The amount of liposome used for lipofection is about 50% of its toxic concentration.

To prepare plasmid/liposome complexes for aerosol gene delivery to lung tissue, cationic liposomes are made containing cationic lipid preparation of 1:1 DOTMA/DOPE (i.e. 1:1 of N-[1-(2,3-dioleyloxy)propyl]-N,N,N-triethylammonium (DOTMA) and dioleoyl phosphatidyle-thanolamine (DOPE). Stock solutions of lipids are dissolved in chloroform and stored under argon at 20° C. Lipids are mixed in round bottomed flasks and evaporated to dryness on a rotary evaporator under reduced pressure. Final lipid concentrations of 10 mM each are made by adding double-distilled water. The resulting mixture is sonicated for about 20 minutes. Between 5 and 50 mg, preferably 12 mg of plasmid is complexed to between 5 and 100 µmol, preferably 24 µmol of DOTMA/DOPE liposomes, which then can be aerosolized. For example, 6 mg of plasmid DNA and 12 µmoles of DOTMA/DOPE liposomes are diluted to 8 ml with water and mixed. Equal volumes are placed in two nebulizers. Subjects are exposed to an air flow rate adequate to generate an aerosol. Approximately between 10 and 120 minutes, preferably 90 minutes, are required to aerosolize the volume dosage.

DNA encoding MT, MnSOD and/or γ-GTP is transfected intratracheally using the lipofection protocol and an expression vector. Suitable expression vectors contain a promoter, such as human beta-actin promoter in pHB APr-1. When testing the efficiency of liposome transfection, a solution of naked-DNA, at the same concentration as that used in the liposome preparation, serves as the control. After transfection, a biopsy of the transfected tissue is tested for: (1) immunoreactive MT, MnSOD and/or γ-GTP, as measured by immunoprecipitation or Western blotting, and (2) function MT, MnSOD and/or γ-GTP activity.

EXAMPLE 6
Protection of Normal Lung Tissue from Ionizing Radiation and Alkylating Agents Rats, mice or other small animals that transiently express recombinant MT, MnSOD, γ-GTP or a combination of these proteins, are tested for the recombinant protein(s)' affect on pulmonary destruction. The protocols disclosed above for introduction of MT, MnSOD, and/or γ-GTP encoding DNA into the lung by liposome, adenovirus vector or ligand-DNA complex can be used to produce the experimental rats expressing the desired recombinant protein in their lungs. Administration to the lung can be via the various routes known to those of skill in the art, preferably injection or inhalation.

Animals are administered the recombinant vector by injection or inhalation between approximately 1 and 14 days, but preferably 2 days, prior to the initiation of the single fraction or fractionated irradiation. In humans being treated for lung cancer, this would be the 6–7 weeks of ionizing radiation treatment, preferably external beam radiation, or the 1–2 weeks of administration of an alkylating agent. Re-administrations are delivered every 2–3 days in the case where multiple weeks of therapy are to be given and where continuous expression over that interval is required. For all experiments, two groups of controls are used: (1) non-transgene expressing animals that are not irradiated and not exposed to an alkylating agent and (2) a group of irradiated or drug treated animals transfected with the vector alone, which does not contain the MT, MnSOD or γ-GTP-encoding gene.

Animals exposed to ionizing radiation to the lung receive a dose of hemi-body irradiation delivering about 500 to 1000 cGY in one fraction or about 2000 to 3000 cGY in multiple fractions. These regimens produce acute radiation pneumonitis in two to three days of the single fraction delivery. Typically, a dose of about 1000 cGY on one day or about 500 cGY on each of three days will produce radiation pneumonitis in laboratory rodents. Humans receive a dose of about 3,000 to 4,000 cGy to the lung over the 6–7 weeks delivery of about 6,000 to 7,000 cGY to a lung cancer. At serial time points after irradiation between about one day and sixty days after irradiation, the animals are sacrificed and the irradiated and control lungs are removed. Techniques well known to those of skill in the art can be used to assess and score lung damage by radiation induced changes. Rubin et al., CLINICAL RADIATION PATHOLOGY, VOLUME 1 (W. B. Saunders, Philadelphia, 1968). For example, histopathological comparisons of the irradiated and control lung quantitate each of the following: (1) the radiation induced changes in the microvasculature, (2) the radiation induced changes in the alveolar cells, (3) acute and sub-acute pulmonary edema, (4) acute and sub-acute pneumonitis, and (5) infiltration of inflammatory cells.

In animals exposed to an alkylating agent, the animals receive a therapeutic dose via the typical route of administration of the alkylating agent, each of which are well known to those of skill in the art. Chabner et al., supra. The alkylating agents used include: cyclophosphamide, nitrogen mustard, melphalan, chlorambucil, busulfan, nitrosourea, cis-platinum, streptozotocin, aziridinylbenzoquinone (AZQ), dicarbazine (DTIC), mAMSA and mitoxantrone. For example, 400 mg/m$^2$ of cyclophosphamide is administered intravenously every day for 5 days; 1–3 mg/mm$^2$ of chlorambucil is administered by a daily or weekly oral administration of about 5 to 10 mgs/liter$^2$; 20–100 mg/mm$^2$ of cis-platinum is administered intravenously every day for 5 days. At serial time points after exposure to the alkylating agent, preferably between about one day and sixty days after exposure, the animals are sacrificed and the exposed tissues are removed. Techniques well known to those of skill in the art can be used to assess and score tissue damage and cell survival by alkylating-induced changes. Rubin et al., supra. For example, histopathological comparisons of the alkylating agent-exposed and control tissue will illustrate relative cell survival.

EXAMPLE 7
Protection of Normal Bladder and Rectal Tissue from Ionizing Radiation and Alkylating Agents Animals receive either an intravesicular or intrarectal instillation of liposomes containing DNA capable of directing the synthesis of MT, MnSOD and/or γ-GTP to protect the bladder epithelium or the rectal mucosa against radiation damage during prostate, ovarian or bladder cancer radiotherapy or during intracavitary cesium applications for cervical or endometrial cancer. Animals receive intravesicle infusion or local enema with DNA-containing liposomes 24 hours prior to instillation of the cesium source or radiotherapy.

Rats that transiently express recombinant MT, MnSOD, γ-GTP or a combination of these proteins, are tested for the recombinant protein(s)' effect on bladder or rectum destruction. The protocols disclosed above for introduction of MT, MnSOD, and/or γ-GTP encoding DNA into the bladder or rectum by liposome, adenovirus vector or ligand-DNA complex can be used to produce the experimental rats expressing the desired recombinant protein in their bladder or rectum.

Animals or human patients are administered the recombinant vector by infection or instillation between approximately 1 and 14 days, but preferably 2 days, prior to and every 2–3 days thereafter, either the 40 to 50 hour low dose rate delivery of about 6,000 cGY of ionizing radiation by intracavitary or interstitial brachytherapy to the endometrium or cervix, or before external beam radiation over 4–6 weeks to an ovarian or prostate cancer patient, or the one to two weeks of administration of an alkylating agent. For all experiments, two groups of controls are used: (1) non-transgene expressing animals that are not irradiated and not exposed to an alkylating agent; (2) a group of irradiated animals transfected with the vector alone, which does not contain the MT, MnSOD or γ-GTP-encoding gene and (3) transgene expressing animals that are not irradiated or exposed to an alkylating agent. Thereafter, the experimental rats or other animals are administered the recombinant vector every two to three days during the radiation or chemotherapy. Typically, a pelvic dose of about 4,000 to 5,000 cGY over 4–5 weeks will produce anterior rectal wall and bladder damage, as measured by symptomatology and/ or cystoscopic or proctoscopic examination. At serial time points after irradiation between about one day and sixty days after irradiation, the animals are sacrificed and the irradiated, alkylating agent and control bladder and rectum are removed. Techniques well known to those of skill in the art can be used to assess and score bladder and rectum damage by radiation. Rubin et al., supra. For example, histopathological comparisons of the irradiated and control bladder and rectum quantitate each of the following: (1) the radiation induced changes in the microvasculature, (2) the radiation induced changes in the epithelial cells, (3) infiltration by inflammatory cells and (4) sites of local infection.

In animals or humans exposed to an alkylating agent, the animals receive a therapeutic dose via the typical route of administration of the alkylating agent, each of which are well known to those of skill in the art and described above. Chabner et al., supra. For example, intracavitary cesium applications for human cervical and endometrial cancer are provided at a dose of about 5000 cGY to the paracervial and obturator nodes over 40 to 50 hours. The posterior bladder wall and anterior rectal wall also get this dose. At serial time points after exposure to the alkylating agent, preferably between about one day and sixty days after exposure, the animals are sacrificed and the exposed tissues are removed. Techniques well known to those of skill in the art can be used to assess and score tissue damage and cell survival by alkylating-induced changes. Rubin et al., supra. For example, histopathological comparisons of the alkylating agent-exposed and control tissue will illustrate relative cell survival.

EXAMPLE 8
Cell Lines Expressing Low Levels of γ-GTP are More Radiosensitive that Cell Lines Expressing Greater Levels of γ-GTP Since gamma-irradiation induces free-radical production and GSH detoxified free radicals, the B16 murine melanoma variants, which demonstrate significant differences in various steps of glutathione metabolism are examined for their sensitivity to ionizing irradiation. In parallel experiments, the high-γ-GTP expressing BL6 cell line was compared to low-γ-GTP expressing B16-F1 cells for their sensitivity to gamma-irradiation killing using a clonagenic in vitro cell survival assay.

Cells of these two lines in exponential growth are harvested by trypsinization, washed and resuspended in culture media. Viability, as determined by trypan blue dye exclusion, is always greater than 90%. Cells are irradiated using a Shepherd $^{137}$Cs irradiator at room temperature. Cells received graded doses of radiation from 0.5 to 10 Gy at a dose rate of 4 Gy/min. After irradiation treatment, cells are plated and incubated for 7 to 10 days at 37° C. Dishes are stained with Crystal violet (2 mg/ml) and colonies of over 50 cells each were counted. Survival curves are generated by computer analysis using a single-hit multi-target model software program.

Figure 4:
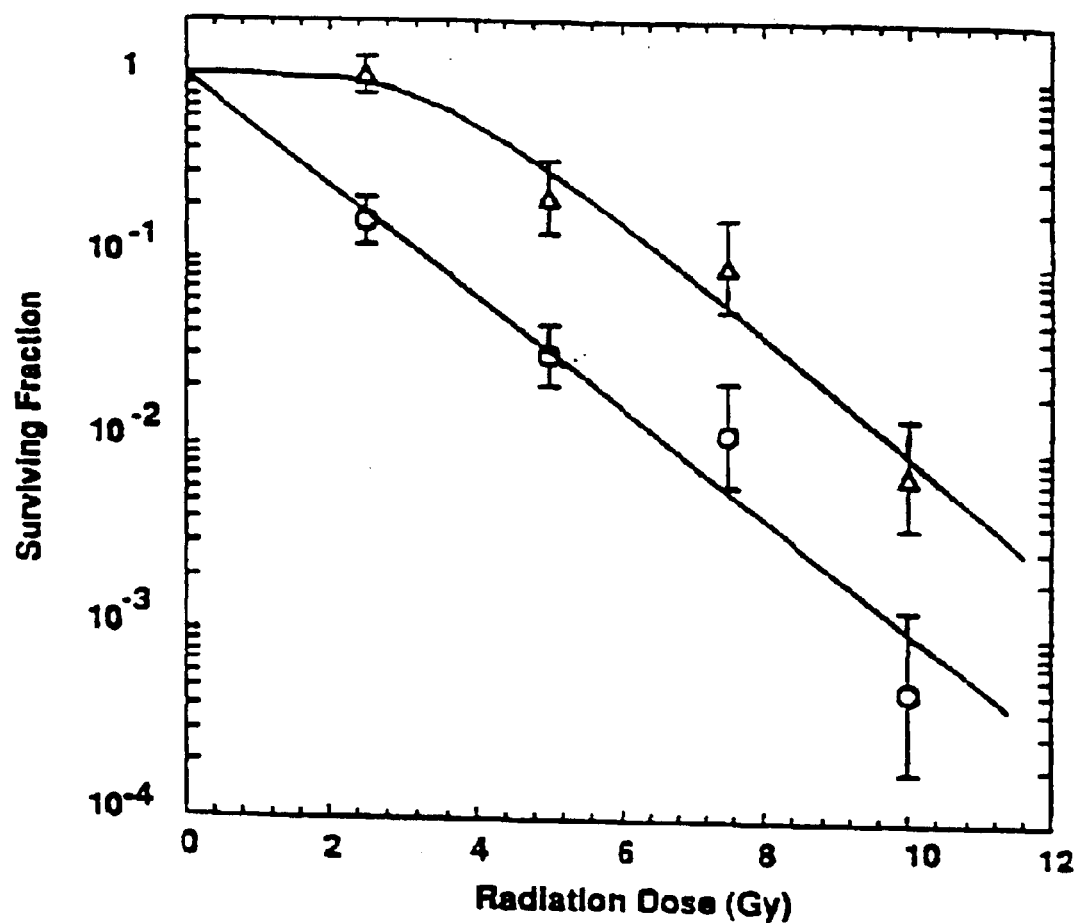
FIG. 4 is a cell survival curve illustrating that a cell line that expresses low levels of γ-GTP (O) exhibits enhanced radiosensitivity relative to a high-γ-GTP expressing cell line (Δ).
Figure 5:
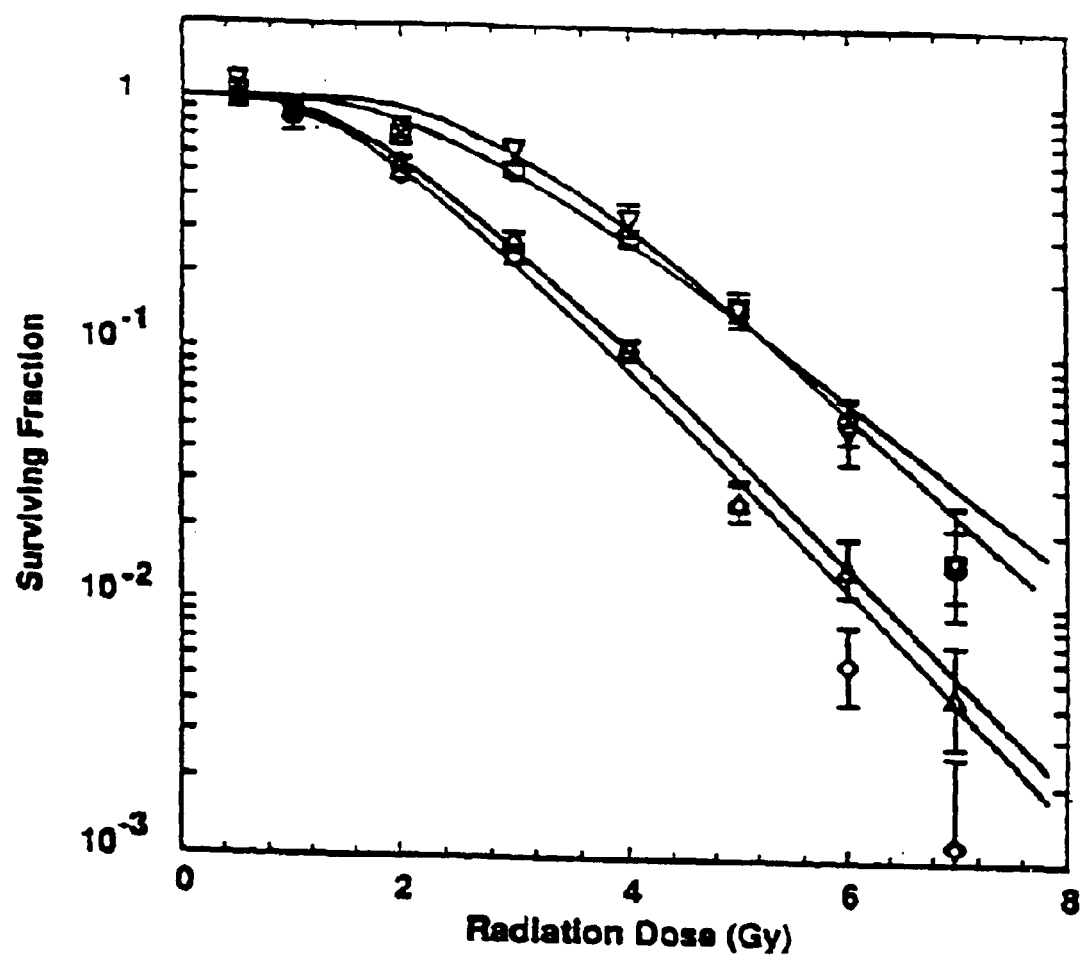
FIG. 5 is a cell survival curve illustrating that the high γ-GTP expressing cell line (upper two curves, Δ and □, showing duplicate experiments) is rendered radiosensitive to gamma irradiation when exposed to a specific inhibitor of γ-GTP (lower two curves, open diamond and Δ, showing duplicate experiments).

FIG. 4 demonstrates that the radiation survival curve of the B16-F1 cell line (open circles) exhibited a diminished capacity, relative to the BL6 cells (open triangles), indicative of decreased repair of damage induced by each dose of gamma-irradiation. These studies demonstrate enhanced radiosensitivity of low-γ-GTP expressing B16-F1 cells relative to high-γ-GTP expressing variant BL6 cells.

We have evidence that protection from radiation provided by recombinant DNA expressing γ-GTP enzyme can differ from cell-line to cell-line. Unlike the murine melanoma cell line B16 described above, human A549 carcinoma cell line and human IB3-1 cell line were not protected by increased levels of γ-GTP activity in transfected cells. Nevertheless, in light of the increased radioresistance exhibited by BL6 cells, the potential remains for use of γ-GTP in radioprotection for cells in tissue other than lung. In the same experiments, the above lung cell lines were protected from radiation by MnSOD, therefore MnSOD is a promising candidate as a protector of lung cells during therapeutic treatment of lung cancers.

Figure 7:
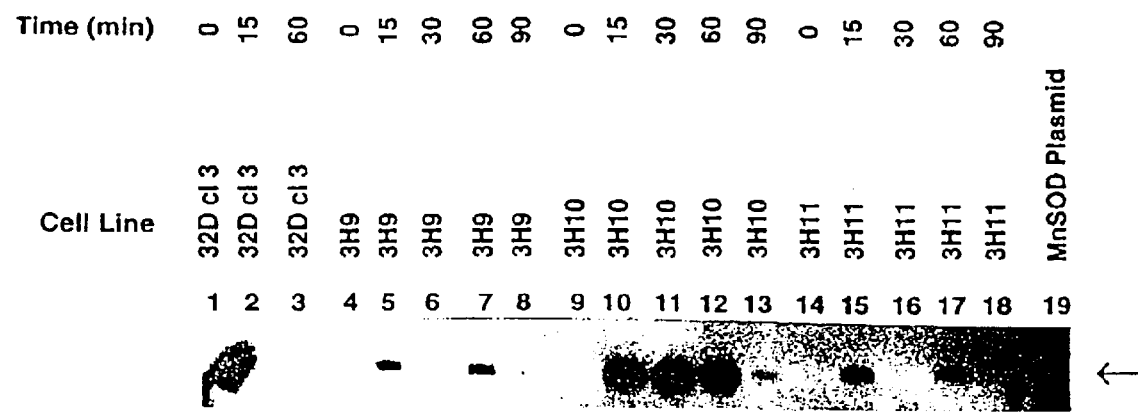
FIG. 7 shows the induction of MnSOD mRNA in 32D MnSOD cell lines by ionizing irradiation. Cells from 32D cl 3, 3H9, 3H10 or 3H11 each received 2000 cGy of irradiation. The mRNA was next extracted at 0, 15, 30, 60, and 90 minutes after irradiation. The mRNA was amplified by RT-PCR. The PCR products were loaded on a 2% agarose gel and analyzed by Southern analysis. Arrow denotes positive fragment size (3H9 is positive at 15, 60 and 90 minutes; 3H10 is positive at 15, 30, 60 and 90 minutes; 3H11 is positive at 15, 60 and 90 minutes.

EXAMPLE 9
The Effect of a γ-GTP Inhibitor on the Radiosensitivity of High and Low γ-GTP Expressing Cell Lines Variant B16 melanoma cell lines are examined for radiosensitivity in the presence or absence of the L-serine-borate complex (4 mM), an inhibitor of γ-GTP. Importantly, serine-borate sensitizes the high-γ-GTP expressing BL6 melanoma cells to gamma-irradiation (FIG. 7). In the presence of serine-borate, the survival of the low γ-GTP expressing cell line, B16-F1 was relatively unchanged (data not shown).

Without further elaboration, it is believed that one skilled in the art can, using the preceding description, utilize the present invention to its fullest extent.

Figure 6:
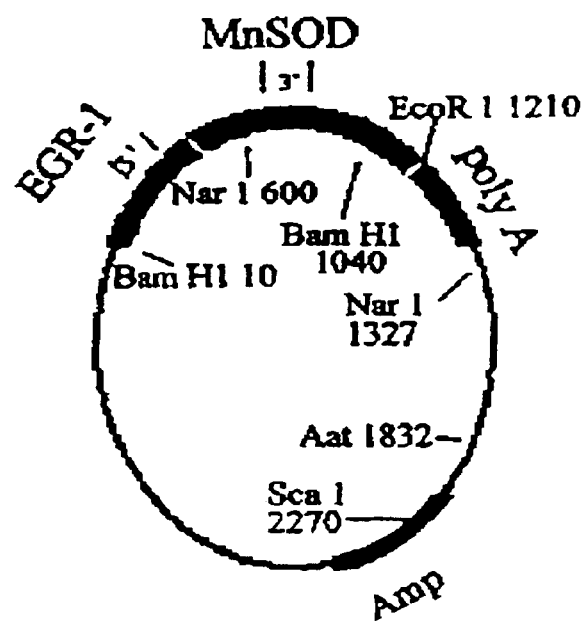
FIG. 6 is a map of plasmid pE425. Plasmid pE425 contains the human MnSOD gene downstream of the erg-1 promoter.

EXAMPLE 10
Expression of a Manganese Superoxide Dismutase Transgene Increases the Radioresistance of 32D CL 3 Hematopoietic Progenitor Cells In order to determine if expression of a manganese superoxide dismutase (MnSOD) transgene protects hematopoietic progenitor cells from ionizing irradiation damage, IL-3-dependent hematopoietic progenitor cell line 32D cl 3 was transfected with a human MnSOD plasmid construct under control of the irradiation inducible egr-1 promoter and co-transfected with the pRSV2-neo plasmid. The plasmid containing the erg-1 human MnSOD gene is pE425 and is shown in FIG. 6.

The 32D cl 3 cell line, derived from a bone marrow culture of a C3H/HeJ mouse, is dependent on IL-3 and demonstrates biologic properties and irradiation sensitivity in vitro similar to that of fresh marrow hematopoietic progenitor cells. (Santucci, M. A.; Anklesaria, P.; Laneuville, P.; Das, I. J.; Sakakeeny, M. A.; FizGerald, T. J.; Greenberger, J. S., "Expression of p210 bcr/abl increases hematopoietic progenitor cell radiosensitivity", *Int. J. Radiat. Oncol. Biol. Phys.* 26:831–836 (1993), Greenberger, J. S.; Sakakeeny, M. A.; Humphries, K. C.; Eaves, C. G.; Eckner, R. J., "Demonstration of permanent factor-dependent multipotential (erythroid/neutrophil/basophil) hematopoietic progenitor cell lines", *PNAS, USA* 80:2931–2935 (1983) and Baffy, G.; Miyashita, T.; Williamson, J. R.; Reed, J. C., "Apoptosis induced by withdrawal of Interleukin-3 (IL-3) from an IL-3-dependent hematopoietic cell line is associated with repartitioning of intracellular calcium and is blocked by enforced bcl-2 oncoprotein production", *J. Biol. Chem.,* 268(9):6511–6519 (1993). The 32D cl 3 cell line was electroporated at 250 volts and 900 μF in the presence of 2 μg of pSV2neo, and either 20, 30 or 40 μg of plasmid containing the pE425 MnSOD plasmid in Hank's Balanced Salt Solution (HBSS). Colonies growing in the presence of 300 μg/ml of G418 were selected, amplified in vitro, and DNA analyzed by Southern blot for the presence of the MnSOD transgene and by reverse transcriptase-polymerase chain reaction (RT-PCR) for MnSOD messenger RNA, by methods described hereinbefore. The Southern blot was probed with a RT-PCR product synthesized by extension of primers specific for the human MnSOD gene. Three clones, 3H9, 3H10 and 3H11 were positive for the presence of the human MnSOD gene.

Irradiation Inducible MnSOD Transgene Transcription in 32D cl 3 Clonal Sublines

We next measured the level of MnSOD mRNA expression from parent 32D cl 3 or each transgene expressing line 3H9, 3H10 and 3H11 cells after stimulation of the radioinducible egr-1 promoter (9-10) by 2000 cGy irradiation. RNA was extracted from aliquots of the irradiated cells at 0, 15, 30, 60 or 90 minutes after irradiation. RT-PCR was performed on the RNA, then Southern analysis was carried out on the extracted DNA. The RNA from each of the lines containing the MnSOD gene was identified in each of the three transgene transfected cell lines. While the transgene was present by Southern analysis of genomic DNA, no message was detected, unless the transfected cell lines were irradiated—see FIG. 7. However, the transgene MnSOD message was detected in each transgene-containing line at 15, 30 and 60 minutes following 2000 cGy of irradiation. By 90 minutes, the level of message was decreased in H9, H10 and H11 [FIG. 7]. The control line 32D cl 3 cells contained no evidence of RNA from the MnSOD transgene—see FIG. 7.

The level of induced MnSOD mRNA was next quantitated in the 3H9 cells by an irradiation dose response analysis. 32D cl 3 and 3H9 cells were irradiated at 0 cGy, 100 cGy×3, 250 cGy×3, 1000 cGy, 1500 cGy and 2000 cGy, to determine what irradiation dose is required for MnSOD mRNA production. RNA was isolated from the cells 30 minutes after irradiation as previously described in the legend to FIG. 2 and amplified by RT-PCR. It was next analysed by Southern analysis where the probe was a P-32-MnSOD PCR fragment. MnSOD transgene induction was greater at the higher doses and peaked at 60 minutes after irradiation. No MnSOD induction was detected in the unirradiated 3H9 cells or in the 32D cl 3 cells under any set of conditions. The data establish that the erg-i promoter is radioinducible in hematopoietic cells in vitro and that transcript levels go down by 90 minutes post induction.

Irradiation Resistance of MnSOD Transgene Overexpressing 32D cl 3 Hematopoietic Cells To determine whether MnSOD expression altered the radioresistance of cells in vitro, the 32D cl 3 parent line, or clonal sublines 3H9, 3H10 or 3H11, were each irradiated at a dose-rate of 100 cGy/min to doses ranging from 0 to 800 cGy. The irradiated cells were plated in methylcellulose and colonies of >50 cells were scored seven days later. The cell lines 3H9, 3H10 and 3H11 were clearly radioresistant compared to the parental cell line 32D cl 3, as reflected in a significantly higher n⁻—see Table 1. The $D_0$ for each transgene expressing cell line was not significantly different from that of parent 32D cl 3 cells. The higher n⁻ of clonal lines 3H9, 3H10 and 3H11 correlated with MnSOD transgene expression and indicated that the cells had an increased capacity to accumulate sublethal irradiation damage compared to 32D cl 3 parental cells.

TABLE 1

Irradiation sensitivity of 32D cl 3 and MnSOD transgene overexpressing sublines

| Cell Line | $D_0$ (cGy) | n⁻ (Gy) |
| --- | --- | --- |
| 32D cl 3 | 189 ± .53 | 1.53 ± .48 |
| 3H9 | 147 ± 0.36 | 7.29 ± 2.04 |
|  | (p = .255) | (p = 0.009) |
| 3H10 | 137 ± .18 | 3.19 ± 0.82 |
|  | (p = .178) | (p = .039) |
| 3H11 | 151 ± .37 | 4.50 ± 2.32 |
|  | (p = .313) | (p = .095) |

Cells from 32D cl 3 or MnSOD overexpressing subclones 3H9, 3H10 and 3H11 were irradiated to doses ranging from 0 to 800 cGy, at a dose-rate of 100 cGy/min. Cells were plated in triplicate cultures of 100 cells/ml, 1000 cells/ml or 5000 cells/ml to semisolid methylcellulose containing medium, and colonies of >50 cells were counted 7 days later. Colony formation was analyzed by linear quadratic and single-hit, multi-target models (Epperly, M. W.; Santucci, M. A.; Reed, J. C.; Shields, D.; Halloran, A.; Greenberger, J. S., "Expression of the human BCL-2 transgene increases the radiation resistance of a hematopoietic progenitor cell line", *Radiation Oncol Invest: Clinical & Basic Res.* 2:77–83, (1994). Results are the mean±S.E.M. of at least three experiments for each cell line, each with a concurrent control.

We conclude that expression of the MnSOD transgene gene may confer significant irradiation resistance to hematopoietic cells, and its regulated expression by irradiation induction at the egr-1 promoter may be useful in conferring relative radioresistance to marrow repopulating cells delivered to bone marrow transplant recipients where further chemotherapy or irradiation is anticipated.

What is claimed is:

1. A method for protecting a subject against an agent that elicits production of a toxic species when said subject is exposed to said agent, wherein said toxic species is selected from the group consisting of a free radical, a superoxide anion, and a heavy metal cation, said method comprising the step of administering to said subject in vivo a pharmaceutical composition comprising
   (A) a polynucleotide that encodes a protein that is transiently expressed in said subject, wherein said protein is capable of neutralizing or eliminating said toxic species; and
   (B) a pharmaceutically acceptable vehicle for said polynucleotide
   wherein said administering is a local administration at the site to be protected from said agent.

2. The method of claim 1, wherein said agent is ionizing radiation.

3. The method of claim 2, wherein said ionizing radiation is clinical radiation therapy.

4. The method of claim 1, wherein said agent is a chemotherapeutic drug.

5. The method of claim 1, wherein said administering is achieved through inhalation.

6. The method of claim 1, wherein said administering is parenteral.

7. The method of claim 1, wherein said administering is intrarectal.

8. The method of claim 1, wherein said administering is intra-vesicle.

9. The method of claim 1, wherein said polynucleotide is a cDNA and said vehicle is a liposome.

10. The method of claim 1, wherein said polynucleotide is a cDNA and said vehicle is an adenovirus vector.

11. The method of claim 1, wherein said polynucleotide is a cDNA and said vehicle is a ligand-DNA conjugate.

12. The method of claim 1, wherein said protein is selected from the group consisting of gamma glutamyl transpeptidase, manganese superoxide dismutase, and metallothionein.

13. The method of claim 1, wherein said protein is gamma glutamyl transpeptidase.

14. The method of claim 1, wherein said protein is manganese superoxide dismutase.

15. The method of claim 1, wherein said protein is metallothionein.

16. The method of claim 1, wherein said pharmaceutical composition comprises a mixture of polynucleotides selected from the group consisting of a polynucleotide encoding gamma glutamyl transpeptidase, a polynucleotide encoding manganese superoxide dismutase and a polynucleotide encoding metallothionein.

17. The method of claim 1, wherein said polynucleotide is under control of an inducible transcriptional regulatory sequence.

18. The method of claim 1, wherein said polynucleotide is under control of a radioinducible transcriptional regulatory sequence.

19. The method of claim 1, wherein said subject is a cancer patient.

20. The method of claim 19, wherein said cancer patient is a lung cancer patient.

21. The method of claim 19, wherein said cancer patient is a prostate cancer patient.

22. The method of claim 19, wherein said cancer patient is a cervical cancer patient.

23. The method of claim 19, wherein said cancer patient is an endometrial cancer patient.

24. The method of claim 19, wherein said cancer patient is an ovarian cancer patient.

25. The method of claim 19, wherein said cancer patient is a bladder cancer patient.

26. The method of claim 1, wherein said administering is performed prior to said subject's exposure to said agent.

27. The method of claim 1, wherein the polynucleotide is stably integrated into the genome in said subject.

28. The method of claim 1, wherein the polynucelotide is not integrated into the genome in said subject.

29. The method according to claim 1, wherein said administering is achieved through intratracheal injection.

* * * * *

UNITED STATES PATENT AND TRADEMARK OFFICE
CERTIFICATE OF CORRECTION

| | | |
|---|---|---|
| PATENT NO. | : 6,887,856 B1 | Page 1 of 1 |
| APPLICATION NO. | : 08/907041 | |
| DATED | : May 3, 2005 | |
| INVENTOR(S) | : Joel S. Greenberger | |

It is certified that error appears in the above-identified patent and that said Letters Patent is hereby corrected as shown below:

Col. 1, line 10, immediately before, "BACKGROUND OF THE INVENTION", insert the following:

--FEDERAL FUNDING STATEMENT

The U.S. Government has certain rights in this invention pursuant to Grant Nos. CA-74918, DK 54225 and AR 45925.--

Signed and Sealed this

Nineteenth Day of September, 2006

JON W. DUDAS
*Director of the United States Patent and Trademark Office*